(12) United States Patent
Ryaby et al.

(10) Patent No.: US 6,355,006 B1
(45) Date of Patent: Mar. 12, 2002

(54) METHOD AND APPARATUS FOR CARTILAGE GROWTH STIMULATION

(75) Inventors: John P. Ryaby, Essex Falls; Roger J. Talish, Hillsborough, both of NJ (US); Emery Rose, Astoria, NY (US); Alan A. Winder, Westport, CT (US); Kenneth Urgovitch, Sr., Clifton, NJ (US)

(73) Assignee: Exogen, Inc., Piscataway, NJ (US)

( * ) Notice: Subject to any disclaimer, the term of this patent is extended or adjusted under 35 U.S.C. 154(b) by 0 days.

(21) Appl. No.: 09/436,999

(22) Filed: Nov. 9, 1999

Related U.S. Application Data

(63) Continuation of application No. PCT/US98/02447, filed on Feb. 6, 1998.
(60) Provisional application No. 60/037,367, filed on Feb. 6, 1997.

(51) Int. Cl.[7] ............................................... A61H 1/00
(52) U.S. Cl. ............................................................ 601/2
(58) Field of Search ............................... 601/2; 600/439

(56) References Cited

U.S. PATENT DOCUMENTS

| | | | |
|---|---|---|---|
| 3,809,977 A | * 5/1974 | Balamuth et al. | ........... 318/116 |
| 4,530,360 A | 7/1985 | Duarte | |
| 5,003,965 A | 4/1991 | Talish et al. | |
| 5,520,612 A | 5/1996 | Winder et al. | |
| 5,524,624 A | * 6/1996 | Tepper et al. | .......... 128/660.03 |
| 5,556,372 A | 9/1996 | Talish et al. | |
| 6,074,352 A | * 6/2000 | Hynynen et al. | .............. 601/3 |

OTHER PUBLICATIONS

Treatment of Osteochondral Defects in Rabbits With SAFHS—Parts I and II, EX1095–01R, EX1096–01R.

* cited by examiner

*Primary Examiner*—William E. Kamm
(74) *Attorney, Agent, or Firm*—Kilpatrick Stockton LLP

(57) ABSTRACT

A kit of elements including an ultrasonic generator, transducers with connecting cables, and a means for locating the transducers over areas of the body containing cartilage, is provided with the surgical instruments for post-surgical application to ultrasonically stimulate the cartilage growth, thus relieving the effects of surgical intervention.

21 Claims, 28 Drawing Sheets

(16 of 28 Drawing Sheet(s) Filed in Color)

METHOD AND APPARATUS FOR CARTILAGE GROWTH STIMULATION

This application is a continuation of International Application No. PCT/US98/02447 filed on Feb. 6, 1998, which application claims priority to a U.S. Provisional Application No. 60/037,367 filed on Feb. 6, 1997.

BACKGROUND OF THE INVENTION

1. Field of the Invention

The present invention relates to methods and apparatus for therapeutically treating injuries using ultrasound. More particularly, the present invention relates to methods and apparatus which utilize an ergonomically constructed ultrasonic transducer assembly configured to cooperate with a placement module for placement in proximity to a cartilage and/or osteochondral injury and/or defect to stimulate cartilage growth.

2. Description of the Related Art

The use of ultrasound to therapeutically treat and evaluate bone injuries is known. Impinging ultrasonic pulses having appropriate parameters, e.g., frequency, pulse repetition, and amplitude, for suitable periods of time and at a proper external location adjacent to a bone injury has been determined to accelerate the natural healing of, for example, bone breaks and fractures.

U.S. Pat. No. 4,530,360 to Duarte describes a basic non-invasive therapeutic technique and apparatus for applying ultrasonic pulses from an operative surface placed on the skin at a location adjacent a bone injury. To apply the ultrasound pulses during treatment an operator must manually hold the applicator in place until the treatment is complete.

The Duarte patent as well as U.S. Pat. No. 5,520,612 to Winder et al. describe ranges of RF signal for creating the ultrasound, ultrasound power density levels, ranges of duration for each ultrasonic pulse, and ranges of ultrasonic pulse frequencies.

U.S. Pat. No. 5,003,965 to Talish et al. relates to an ultrasonic body treatment system having a body-applicator unit connected to a remote control unit by sheathed fiber optic lines. The signal controlling the duration of ultrasonic pulses and the pulse repetition frequency are generated apart from the body-applicator unit. Talish et al. also describes a mounting fixture for attaching the body-applicator unit to a patient so that the operative surface is adjacent the skin location.

While the systems described in these patents relate to therapeutic methods and apparatus for ultrasonic treatment of hard and soft tissue injuries and defects, there is a need for ergonomically configured signal generators and transducers for the treatment of cartilage and/or osteochondral injuries and/or defects. Further, a need exists for an apparatus which optimizes the treatment of cartilage and/or osteochondral injuries and/or defects.

A cartilage and/or osteochondral injury and/or defect typically involves damage to the cartilage which lines articulating bones (articular cartilage), such as the bones of the knee, elbow, shoulder and ankle. Osteochondral injuries can be treated by chondral and/or osteochondral drilling causing blood flow at the site. The aim of chondral drilling is to stimulate cartilage regeneration as part of the healing process. However, the resulting nonhyaline or fibrocartilage produced is biomechanically inferior to articular cartilage, does not have comparable proteoglycan content, and may consist primarily of a thin unorganized layer of collagen. Further, it has been observed that degeneration of the new tissue generally occurs over time, requiring the need for additional reconstructive surgical treatment.

Other methods of treatment include: the transplantation of non-weight bearing cartilage to the injury and/or defect site; inducing a fracture at the injury and/or defect site; placing a carbon fiber matrix to induce cartilage formation; and autologous chondrocyte implantation (ACI). ACI entails removing chondrocytes capable of regenerating hyaline-like cartilage from the body and culturin them for several weeks. During the culture process, the number of cells increases approximately 15 times that of the original tissue sample. The cultured cells are then transplanted through an arthrotomy. A small piece of periosteum, the skin covering a bone, is taken from the patient's tibia. The periosteum is then sutured over the defect to provide a protective cover for the cultured cells. The cultured cells are injected under the periosteum into the defect where they will continue to multiply and produce a durable repair tissue. However, ACI increases the healing time since the chondrocytes need to be cultured before they are transplanted to the patient.

Therefore, there is a further need for a method and apparatus to stimulate cartilage regeneration which produces fibrocartilage which is biomechanically equal or superior to articular cartilage, has comparable proteoglycan content, and consists of a thick organized layer of collagen. Further still, a need also exists for an apparatus which stimulates cartilage regeneration and where the regenerated cartilage does not degenerate over time requiring additional treatment or reconstructive surgery. Further, there is a need for an apparatus which stimulates cartilage regeneration and significantly reduces the healing time.

SUMMARY OF THE INVENTION

The ultrasonic treatment apparatus of the present invention is used for therapeutically treating cartilage and/or osteochondral injuries and/or defects using ultrasound. The apparatus includes an ergonomically constructed placement module configured for mounting at least one ultrasonic transducer assembly with an integral signal generator which provides excitation signals to at least one ultrasonic transducer within the transducer assembly. Timing control circuitry as well as monitoring circuitry for the proper attachment and operation of the transducer assembly are housed within a portable main operating unit which may be fit within a pouch worn by the patient. In operation, the placement module is positioned against a part of the patient's body such that at least one trasducer is positioned over the cartilage and/or osteochondral injury and/or defect. At least one transducer is then excited for a predetermined period of time to impinge ultrasonic waves against the damaged cartilage area to stimulate the regeneration of new articular cartilage.

Preferably, the main operating unit has an internal power source for powering the signal generator circuitry, a display coupled to the signal generator circuitry to display treatment sequence data, a keypad coupled to the signal generator circuitry to permit user operation and/or entry of data. The signal generator circuitry includes a processor, means for generating a pulsed control signal, and a switch coupled to the processor for regulating the pulsed control signal. A communication interface may be connected between a communication port and the processor to provide a communication link between the ultrasonic signal generator and an external computer or modem. Preferably, the communication interface is a serial communication interface, however, a parallel interface is also contemplated. An alarm is provided to indicate to the user that the treatment time has expired. The alarm is coupled to the processor such that when ultrasonic treatment is completed the processor activates the alarm and terminates ultrasound generation.

The present invention also provides a kit for ultrasonically treating cartilage and/or osteochondral injuries and/or defects. The kit includes an ultrasonic transducer assembly, a placement module configured to be worn by a patient and to receive the ultrasonic transducer assembly, an integrated ultrasonic signal generator located in the ultrasonic transducer assembly, and a main operating unit (MOU) or controller. The MOU has an internal power source thereby providing patient mobility. A MOU envisioned for use with the present invention is described in U.S. Pat. No. 5,556,372 to Talish et al. which is hereby incorporated by reference.

The MOU is electrically coupled to at least one transducer secured to the placement module. The activation of the signal generator corresponding to each transducer excites at least one ultrasonic transducer for impinging ultrasonic waves to the cartilage and/or osteochondral injury and/or defect.

A method for ultrasonically treating cartilage and/or osteochondral injuries and/or defects is also provided. Once the location of the cartilage and/or osteochondral injury and/or defect is ascertained, the body's own natural healing processes are stimulated adjacent the injury. This can be accomplished by chondral drilling on the defect to form a series of channels to stimulate blood flow and induce the biological reconstructive healing response of the underlying area at the cartilage site. Other methods of stimulating this response includes laser drilling, induce fracture, scraping, chemical or biochemical treatments, etc. Once the healing response has been sufficiently facilitated, a placement module containing an ultrasonic transducer assembly having at least one transducer and one signal generator is positioned adjacent to the injured part of the body such that at least one transducer is in proximity to the cartilage and/or osteochondral injury and/or defect for the treatment of the injury. The signal generator is then activated to excite the at least one transducer for impinging ultrasonic waves to the cartilage and/or osteochondral injury and/or defect. The ultrasonic waves impinge upon the injury site to stimulate and accelerate the biological healing properties of the body to regenerate cartilaginous material. The present method can also be used in conjunction with the transplantation of autologous cultured chondrocytes to the injury site to increase the healing time.

In an alternative embodiment, a placement module is provided for securing a plurality of transducers thereto in a plurality of configurations. The placement module is then secured to a cartilage and/or osteochondral injury and/or defect site, for example, at the ankle or wrist, to stimulate cartilage regeneration. Further, the present invention also provides an embodiment having a placement module which contains a locking structure for locking the articulating bones in a particular position. This embodiment prevents the patient from moving his limbs, for example, moving the femur with respect to the tibia, during treatment.

BRIEF DESCRIPTION OF THE DRAWINGS

Preferred embodiments of the invention are described below with reference to the drawings, which are described as follows.

The file of this patent contains FIG. 13A through FIG. 19D which are executed in color. Copies of this patent with color drawings will be provided by the Office upon request and payment of the necessary fee.

DETAILED DESCRIPTION OF THE PREFERRED EMBODIMENTS

The ultrasonic treatment apparatus of the present invention is used for the surgically non-invasive utilization of ultra high-frequency acoustic energy in the treatment of cartilage and/or osteochondral injuries and/or defects. Even though this detailed description discusses the treatment of cartilage and/or osteochondral injuries and/or defects caused by an injury, the ultrasound treatment apparatus can be used to treat osteochondral defects caused by other means, such as medication, infection or metabolic processes.

The apparatus includes an ergonomically constructed placement module having a strap or other fastening means for being secured adjacent an injured part of a patient's body. At least one ultrasonic transducer assembly is attached or imbedded within the placement module and properly positioned in proximity to the cartilage and/or osteochondral injury and/or defect. Different types of ultrasonic transducers and signals can be provided, such as those described and schematically depicted in U.S. Pat. No. 5,520,612 to Winder et al. which is hereby incorporated by reference. Particularly, the transducers and arrangements schematically depicted by FIGS. 7–11 of the patent in which at least one transducer is used to provide acoustic energy to the site of the injury. The apparatus may also utilize a portable, ergonomically constructed main operating unit (MOU) worn by the patient which provides control signals to the ultrasonic transducers. The MOU which is utilized is preferably the one described in U.S. Pat. No. 5,556,372 to Talish et al. which is hereby incorporated by reference.

Figure 1:
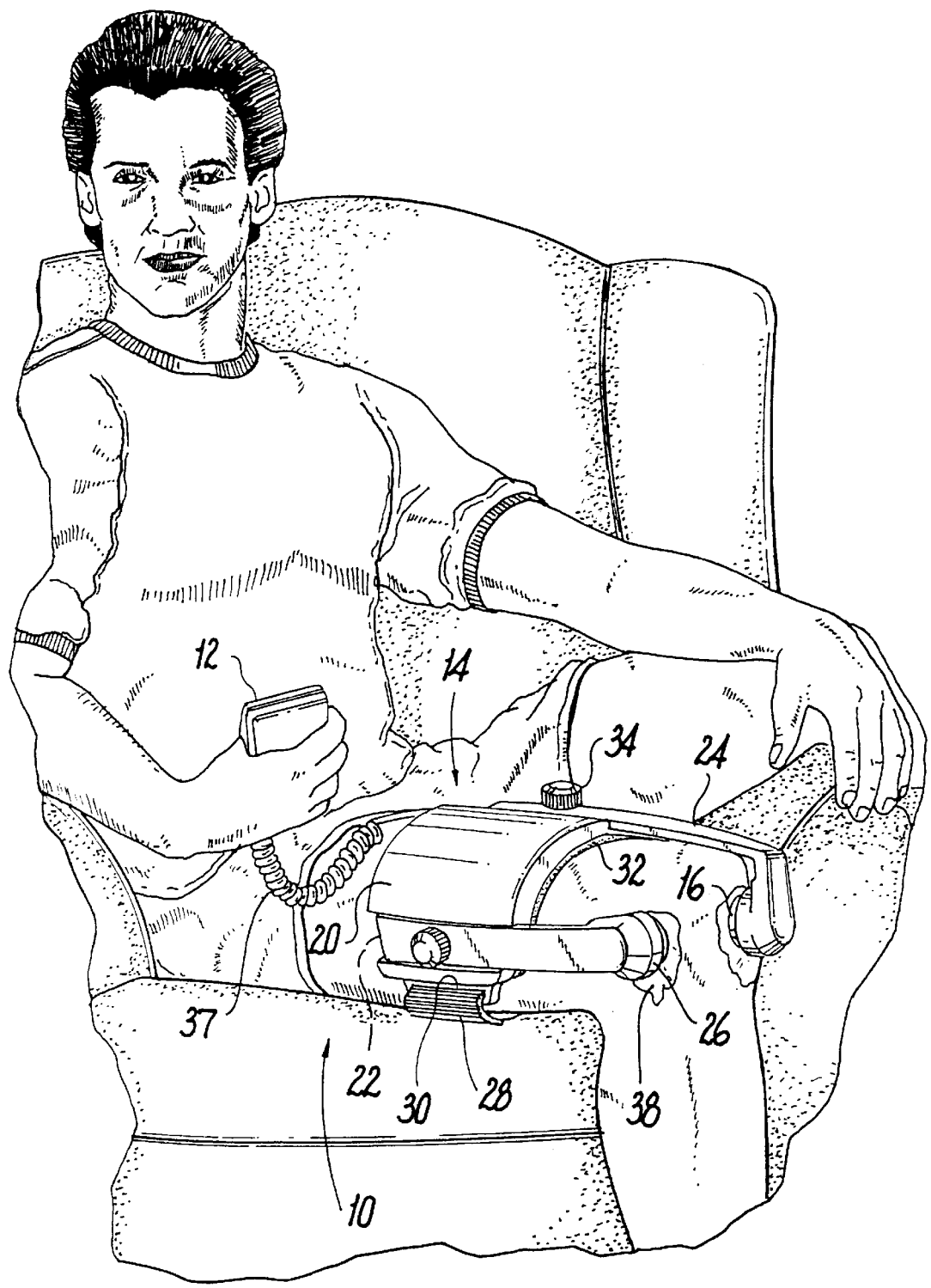
FIG. 1 is a perspective view of a patient wearing a portable ultrasonic treatment apparatus of a first embodiment according to the present invention having a main operating unit or controller and a placement module.

Turning to the figures, in particular FIG. 1, one embodiment of the portable ultrasonic treatment apparatus 10 of the present invention is shown. The ultrasonic treatment apparatus 10 includes a MOU 12, a placement module 14, and ultrasonic transducer assemblies 16.

The placement module 14 comprises a placement support 20 which includes at least two or three channels 22 each having an extension 24 mounted therein. Each extension has a transducer pocket 26 at one end for holding one ultrasonic transducer assembly 16. It is contemplated for each extension 24 to have several range of movements besides longitudinal motion, such as articulating motion transverse to the longitudinal motion.

Figure 2A:
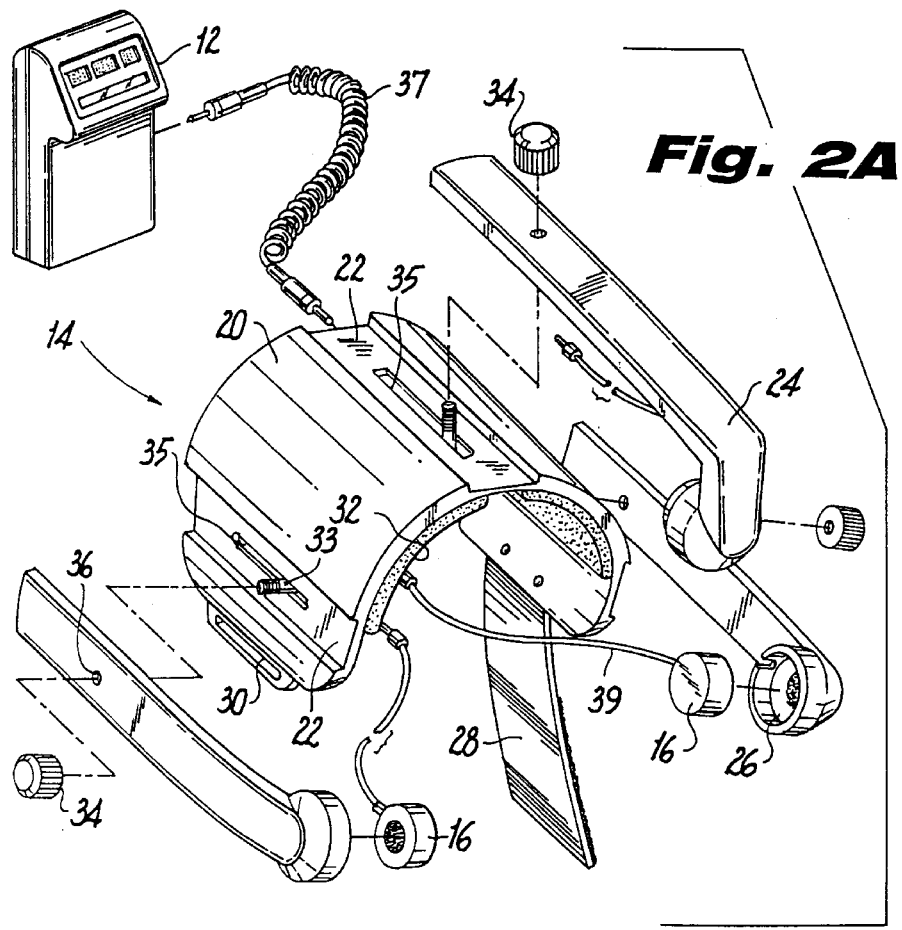
FIG. 2A is an exploded view of the placement module of the portable ultrasonic treatment apparatus illustrated by FIG. 1.
Figure 2B:
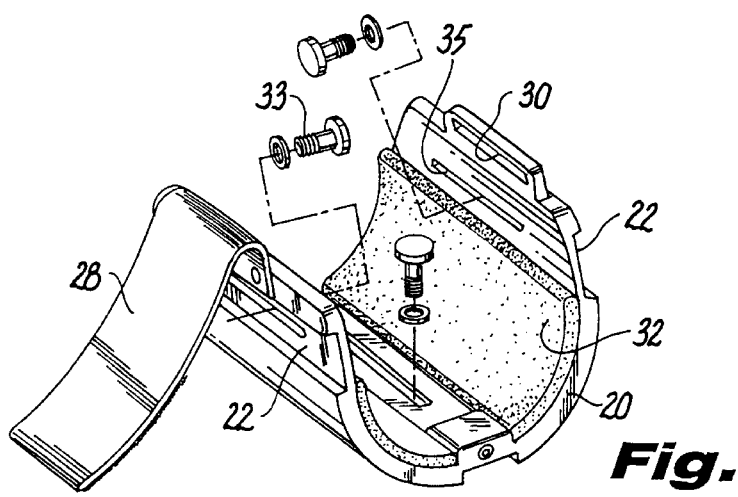
FIG. 2B is a rear underside view of the placement module of the portable ultrasonic treatment apparatus illustrated by FIG. 1.

The placement module 14 further includes a placement band 28 cooperating with slot 30 for securing the placement support 20 to the patient. The placement band 28 is configured to firmly secure the placement module 14 to the patient. A sponge-like material 32 preferably lines the inner surface of the placement support 20 for providing comfort to the patient (FIGS. 2A and 2B). The placement support 20 may be constructed of hard plastics which may be custom molded for a particular body part of the patient.

With reference to FIGS. 2A and 2B, the extensions 24 are mounted to the placement support 20 via screws 33 and thumb screws 34. The screws 33 are passed through slots 35 and holes 36 on the extensions 24 and are threaded to the thumb screws 34. The extensions 24 can be moved to different positions to accommodate patients of all sizes by unthreading the thumb screws 34 and shifting the screws 33 along the slots 35 and threading the screws 33 to the thumb screws 34 at the new position.

The transducer assembly 16 may include circuitry, schematically illustrated by FIGS. 4 and 4A and described below, for exciting at least one transducer therein and is coupled to the MOU by cable 37 and wires 39. The wires 39 are coupled to the placement support 20. The cable 37 is preferably a multiconductor cable capable of transmitting relatively low frequency RF or optical signals, as well as digital signals. The cable 37 may include coaxial cable or other types of suitable shielded cable. Alternatively, the cable 37 may include fiber optic cable for transmitting optical signals. The signals may be transmitted continuously or as a series of pulses.

Figure 3:
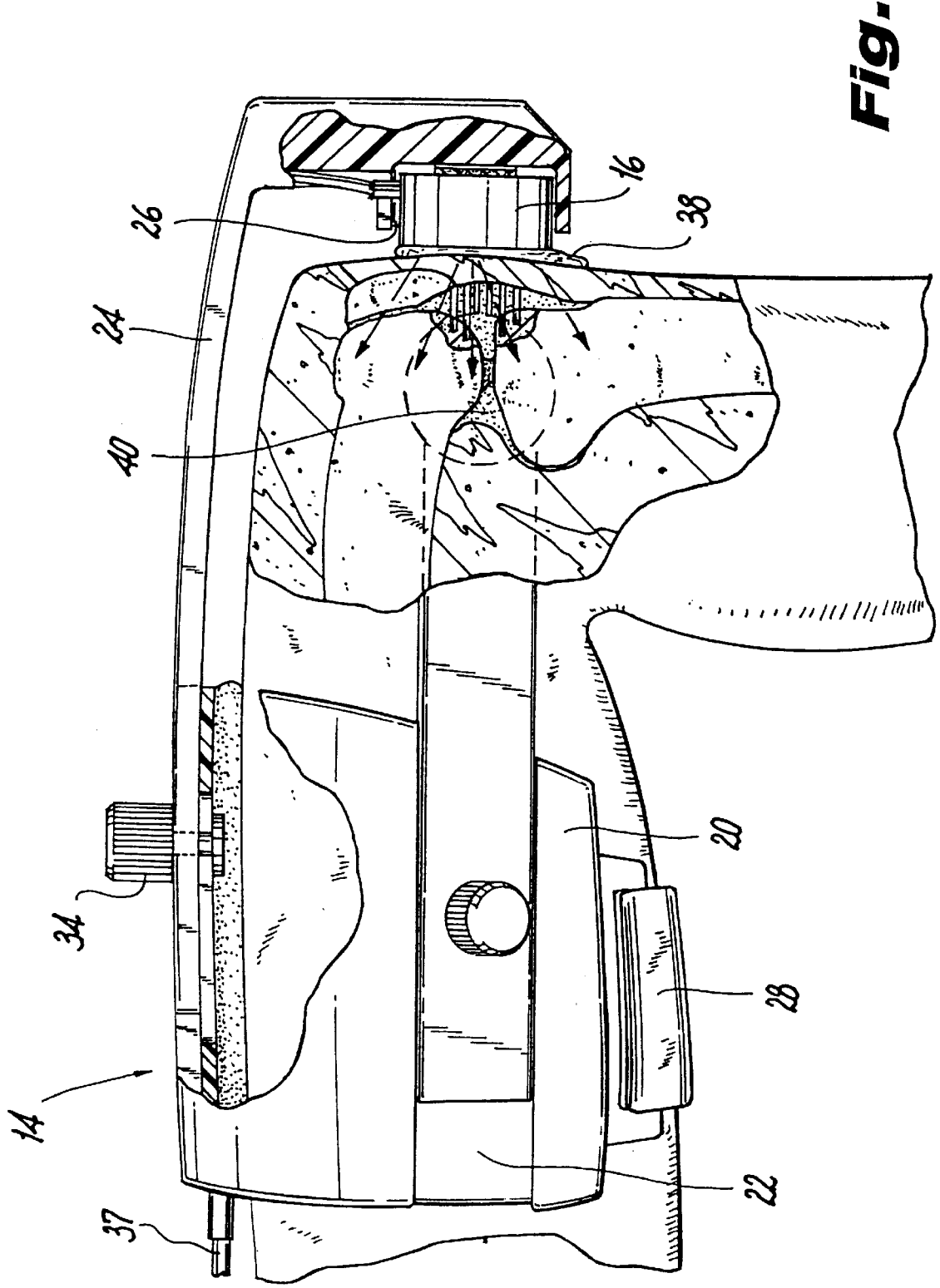
FIG. 3 is a cross-sectional view illustrating the transducer assembly impinging ultrasonic waves to articular cartilage within the knee where an ultrasonic conducting gel is positioned between the transducer assembly and the patient's knee.

In operation, the placement module 14 is positioned and secured to the patient's body as shown by FIG. 3, such that each transducer assembly 16 lies over the cartilage and/or osteochondral injury and/or defect. A locating ring such as the one disclosed in U.S. patent application Ser. No. 08/389,148 may be used for determining the location of injured bone, if the patient desires to have one of the transducer assemblies overlying a bone injury, before the placement module 14 is secured to the patient. Once the placement module 14 is properly positioned, the transducer within the transducer assembly 16 is excited for a pre-determined amount of time. An ultrasound conducting gel 38 is positioned between the transducer assembly 16 and the injured part of the patient's body to prevent attenuation of the ultrasonic waves as they travel to the articular cartilage 40, as shown by FIG. 3.

It is also contemplated that one or more transducers can be converted to receive reflected diagnostic data from the treatment site. This permits real time evaluation of the injury site and healing process.

Figure 4:
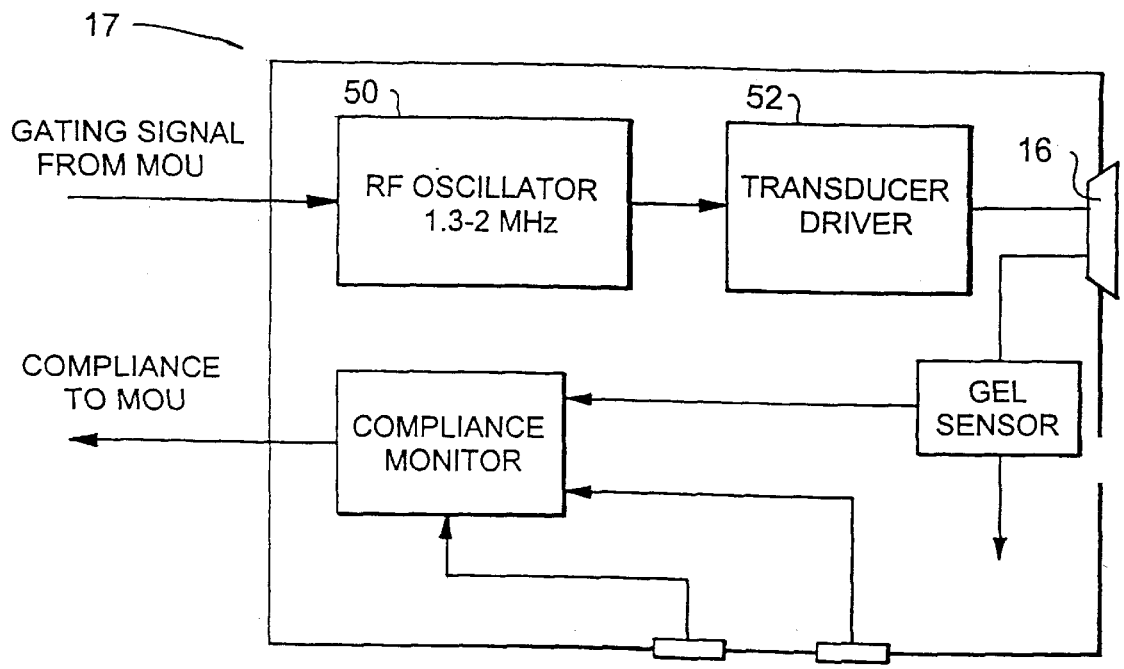
FIG. 4 is a block diagram of one embodiment of the circuitry for the ultrasonic transducer assembly.

With reference to FIG. 4, a block diagram of one embodiment of the ultrasonic transducer assembly circuitry is shown. The transducer assembly circuitry 17 includes a receiver/RF oscillator 50 which receives the signals transferred by a signal generator within MOU 12 via cable 37. The receiver/IRF oscillator 50 is connected to transducer driver 52 which excites transducer 16.

Figure 4A:
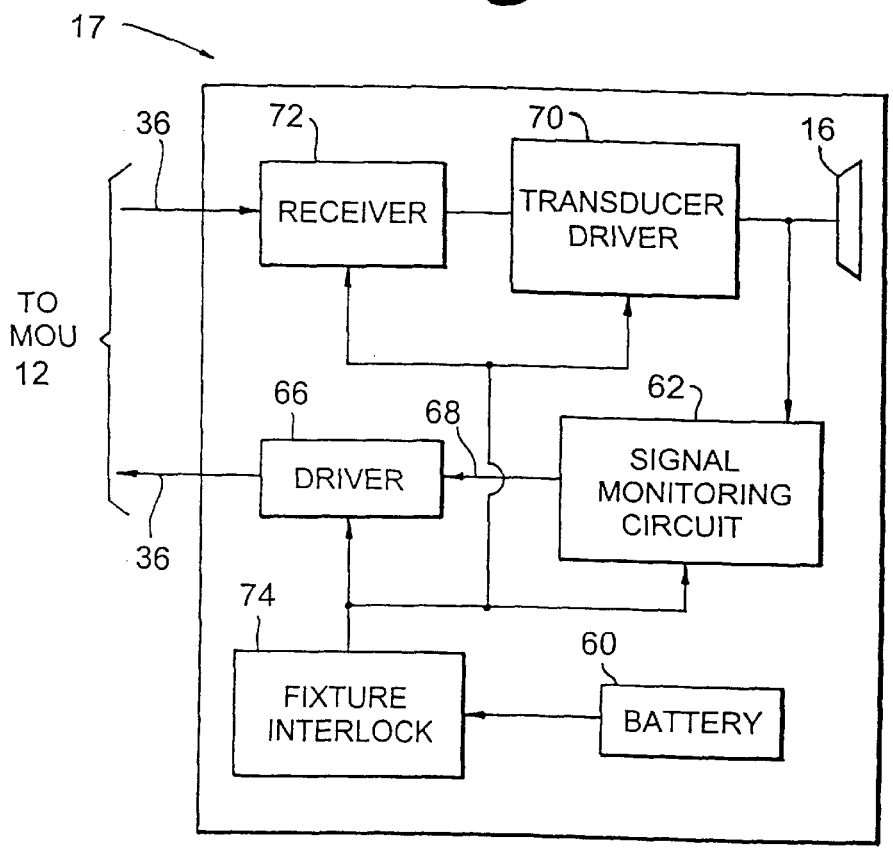
FIG. 4A is a block diagram of an alternative embodiment of the circuitry for the ultrasonic transducer assembly.

An alternative embodiment of the transducer assembly circuitry 17 is shown in FIG. 4A. In this embodiment, the ultrasonic transducer assembly 16 includes an internal battery 60 which supplies power to the components within the transducer assembly 16. For example, battery 60 supplies power to signal monitoring circuit 62 and signal driver 66. The signal monitoring circuit 62 provides, preferably, a digital output signal 68 which represents the waveform characteristics of the output of transducer driver 70. These characteristics can be displayed on a digital display and may include, for example, the frequency, pulse repetition frequency, the pulse width and the average output power of the transducer 16. The output signal 68 of signal monitoring circuit 62 is transferred to the signal generator within MOU 12 via driver 66 and cable 37. The signal generator may include a processor and a switch for regulating the signal characteristics. Control signals from the MOU 12 are received by receiver 72 via cable 37. Safety or fixture interlock 74, which may include switches on the outer surface of the placement module 14 or transducer assembly 16, ensures that the placement module 14 is properly positioned before providing power to the internal components of the transducer assembly 16.

Figure 5:
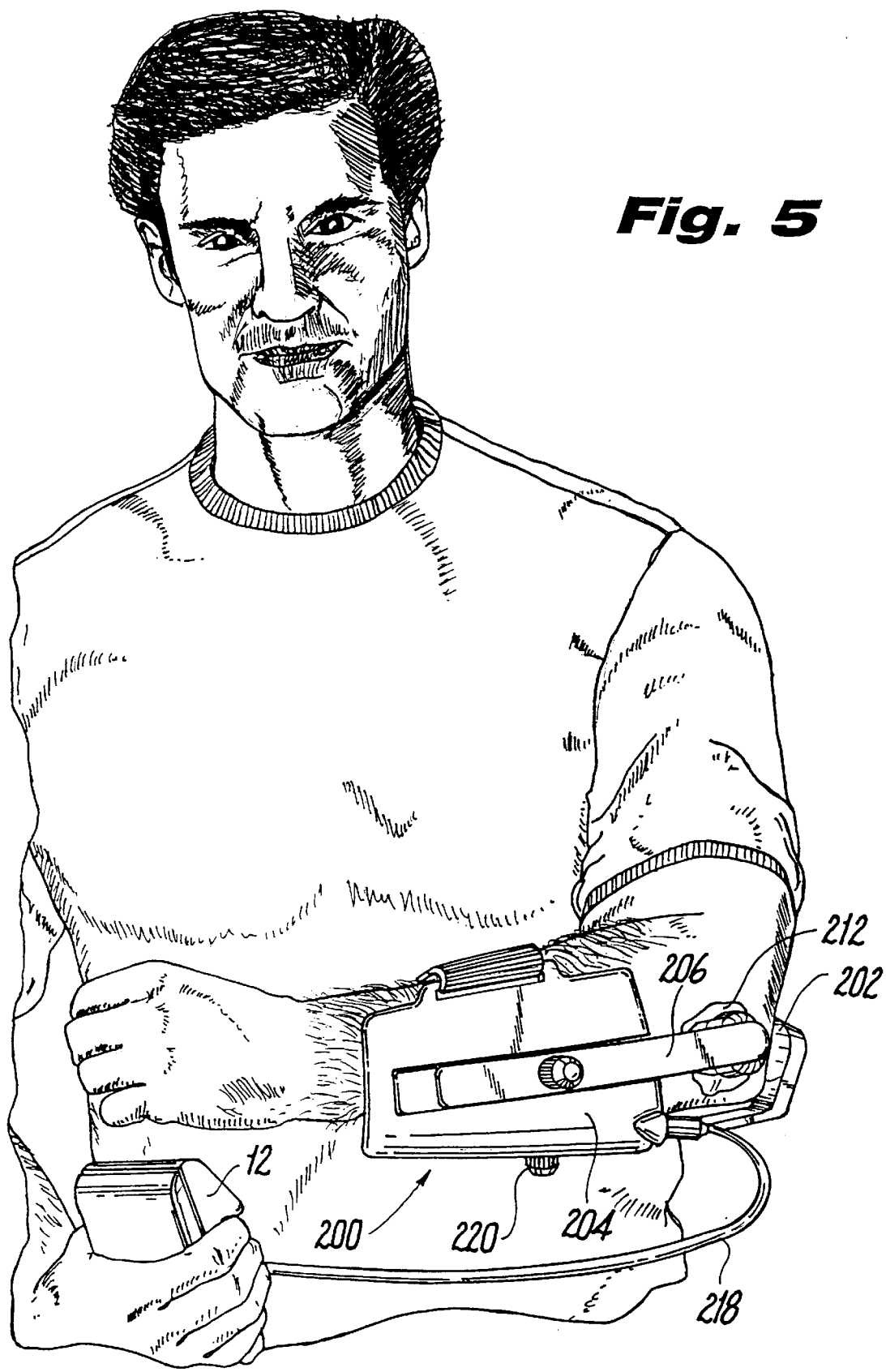
FIG. 5 is a perspective view of a second embodiment of the portable ultrasonic treatment apparatus, illustrating a main operating unit or controller and a placement module for treating osteochondral injuries within the elbow region.

A second embodiment of the portable ultrasonic treatment apparatus of the present invention is illustrated by FIG. 5 and designated generally by reference numeral 200. The treatment apparatus 200 includes MOU 12 and transducer assemblies 202 affixed to a placement module 204 via extensions 206 for ultrasonically stimulating the generation of cartilage in the elbow region. Each transducer assembly 202 includes a power transducer 212 connected to the MOU 12 by cable 218. An ultrasonic conducting gel 212 is positioned between the transducer assemblies 202 and the osteochondral injury to prevent attenuation of the ultrasonic waves as they travel to the articular cartilage. In order to accommodate various patients, the extensions 206 can be adjusted to several positions by unthreading thumb screws 220. The circuitry for each transducer assembly 202 may be similar to that disclosed for the first embodiment and schematically illustrated by FIGS. 4 and 4A.

It is envisioned that the placement module 204 be constructed from suitable conductive plastics, such as conductive ABS plastics with either carbon, stainless steel, nickel or aluminum fibers to forego the use of wires for connecting the transducer assemblies 202 to the cable 218. In such an embodiment, the conductive placement module 204 would be used to electrically connect the transducer assemblies 202 to the MOU 12 via cable 218.

Figure 6:
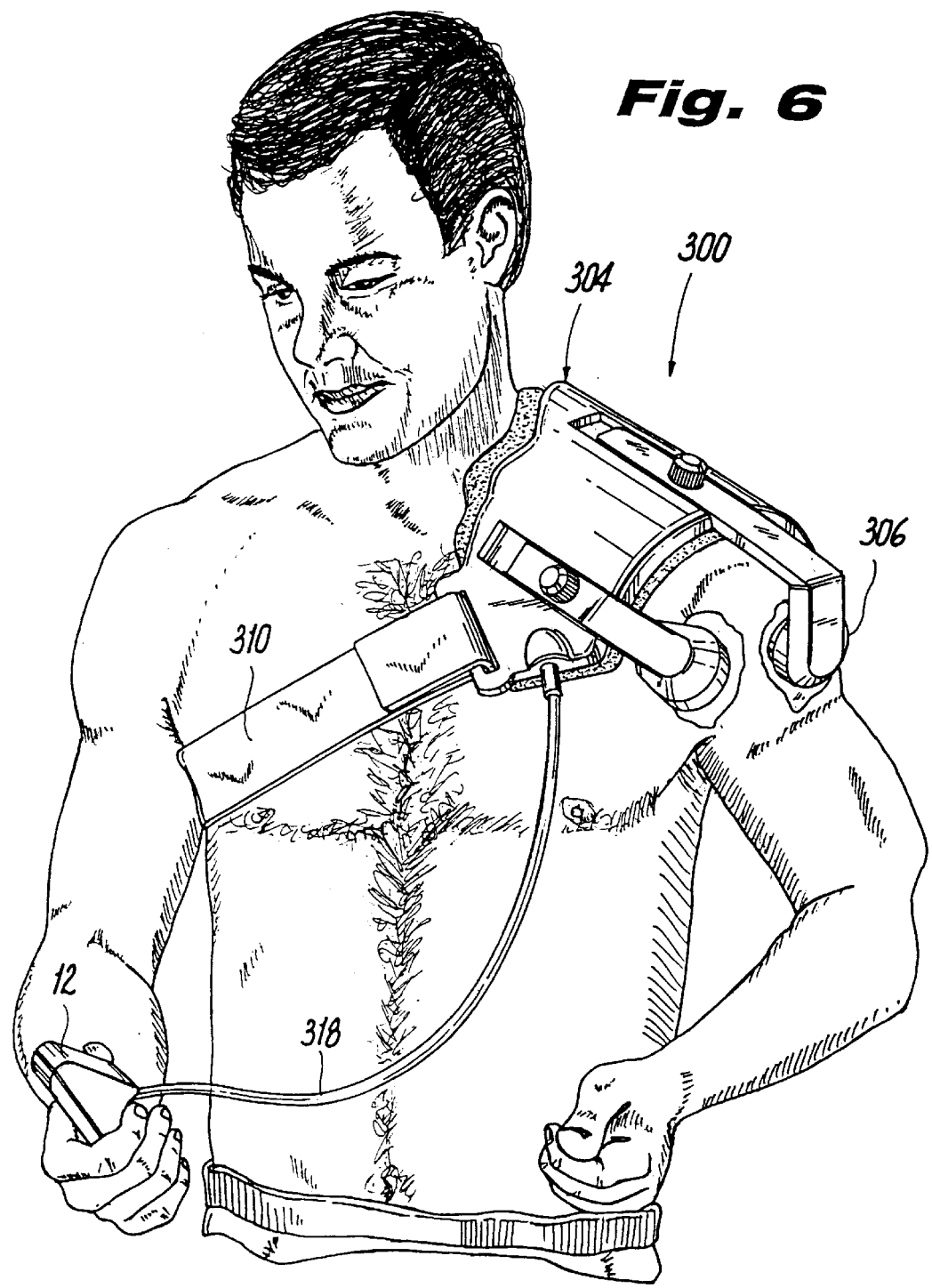
FIG. 6 is a perspective view of a third embodiment of the portable ultrasonic treatment apparatus, illustrating a main operating unit or controller and a placement module for treating osteochondral injuries within the shoulder region.

With reference to FIG. 6, a third embodiment of the portable ultrasonic treatment apparatus of the present invention is illustrated. In this embodiment, the treatment apparatus 300 includes a MOU 12, a placement module 304, and ultrasonic transducer assemblies 306. The placement module 304 is configured for placement on the shoulder region and includes a placement band 310 and a placement support 312. Each transducer assembly 306 is connected to the MOU 12 by cable 318 to power transducer assembly circuitry within each assembly 306. The circuitry (not shown) may be similar to that disclosed for the first and second embodiments and schematically illustrated by FIGS. 4 and 4A.

In operation, transducers within transducer assemblies 306 are excited for a pre-determined period of time to impinge ultrasonic waves to articular cartilage within the shoulder region.

Figure 7:
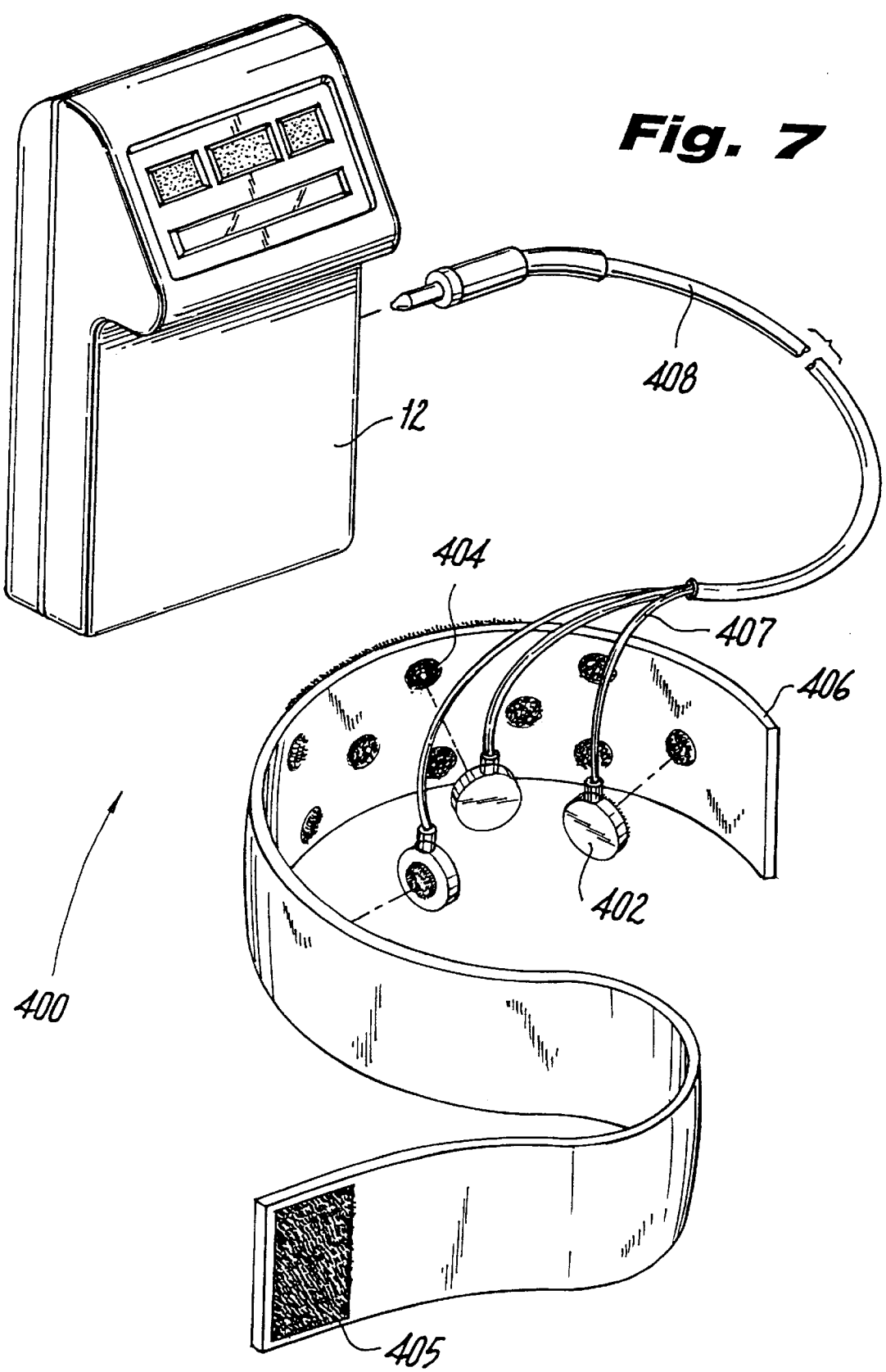
FIG. 7 is a perspective view of a fourth embodiment of the portable ultrasonic treatment apparatus illustrating a main operating unit or controller and a placement module.
Figure 8:
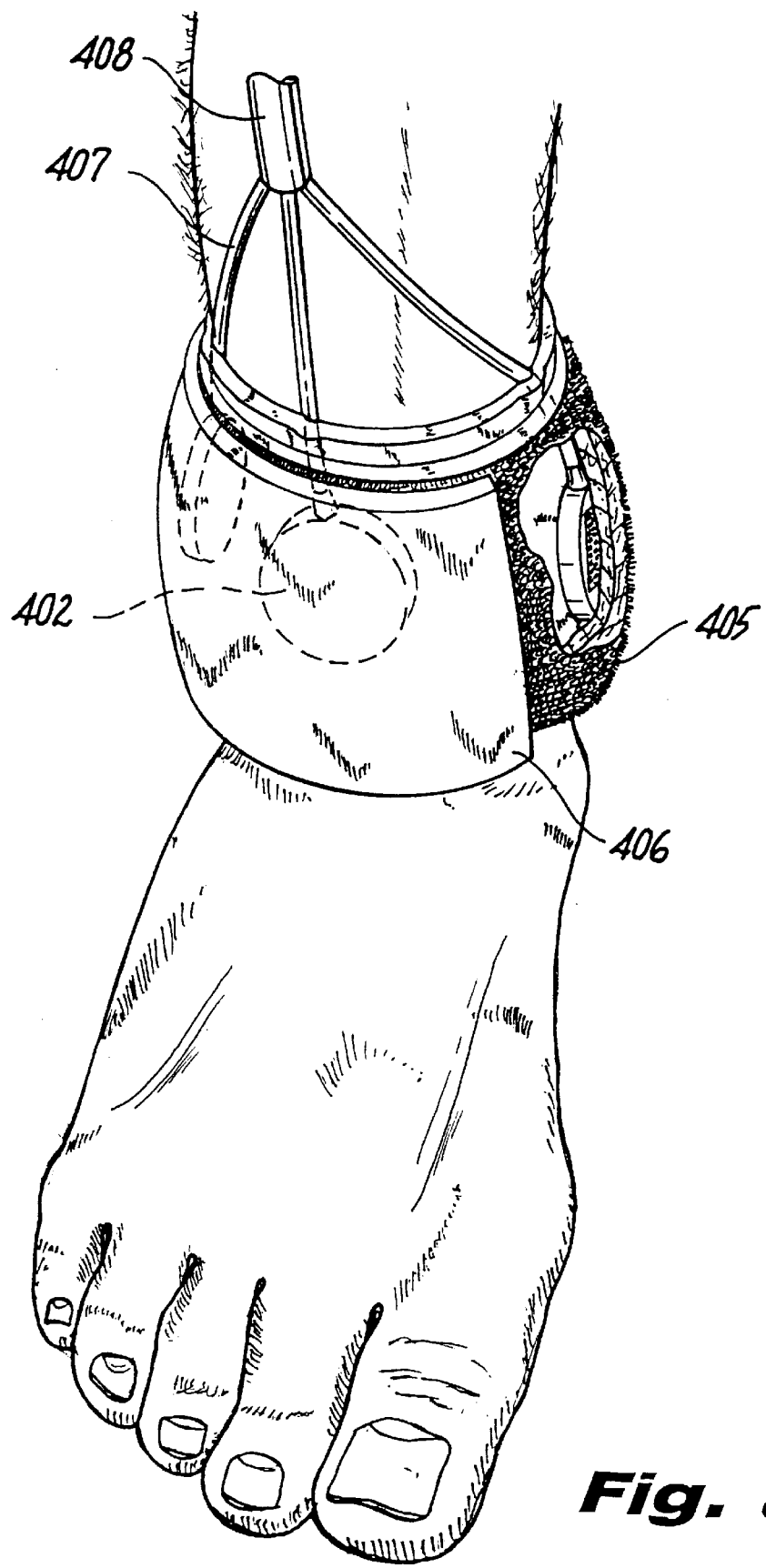
FIG. 8 is a perspective view of the portable ultrasonic treatment apparatus illustrated by FIG. 7 mounted on a patient's ankle.

A fourth embodiment of the portable ultrasonic treatment apparatus of the present invention which is primarily suitable for the treatment of cartilage and/or osteochondral injuries and/or defects is illustrated by FIGS. 7 and 8. In this embodiment, the apparatus 400 includes at least one ultrasonic transducer assembly 402 positioned within pockets 404 on a strip 406. The transducer assemblies 402 may be arranged in a plurality of configurations within pockets 404 to accommodate many patients' anatomical differences. The strip 406 is secured in proximity to a cartilage and/or osteochondral injury and/or defect as shown by W FIG. 8 by a self-tieing material 405. The strip 406 is connected via wires 407 and cable 408 to a MOU 12 which contains circuitry for exciting the at least one ultrasonic transducer assembly 402 affixed to the strip 406.

In operation, at least one transducer assembly 402 is excited to impinge ultrasonic waves to the cartilage and/or osteochondral injury and/or defect as shown by FIG. 8. It is contemplated that during treatment an ultrasonic conducting gel is positioned between the strip 406 and the patient's body to prevent attenuation of the ultrasonic waves.

It is also contemplated to manufacture the strip 406 from suitable conductive plastics such as conductive. ABS plastics with either carbon, stainless steel, nickel or aluminum fibers to forego the use of wires for electrically connecting the at least one ultrasonic transducer 402 to the cable 408.

Figure 9:
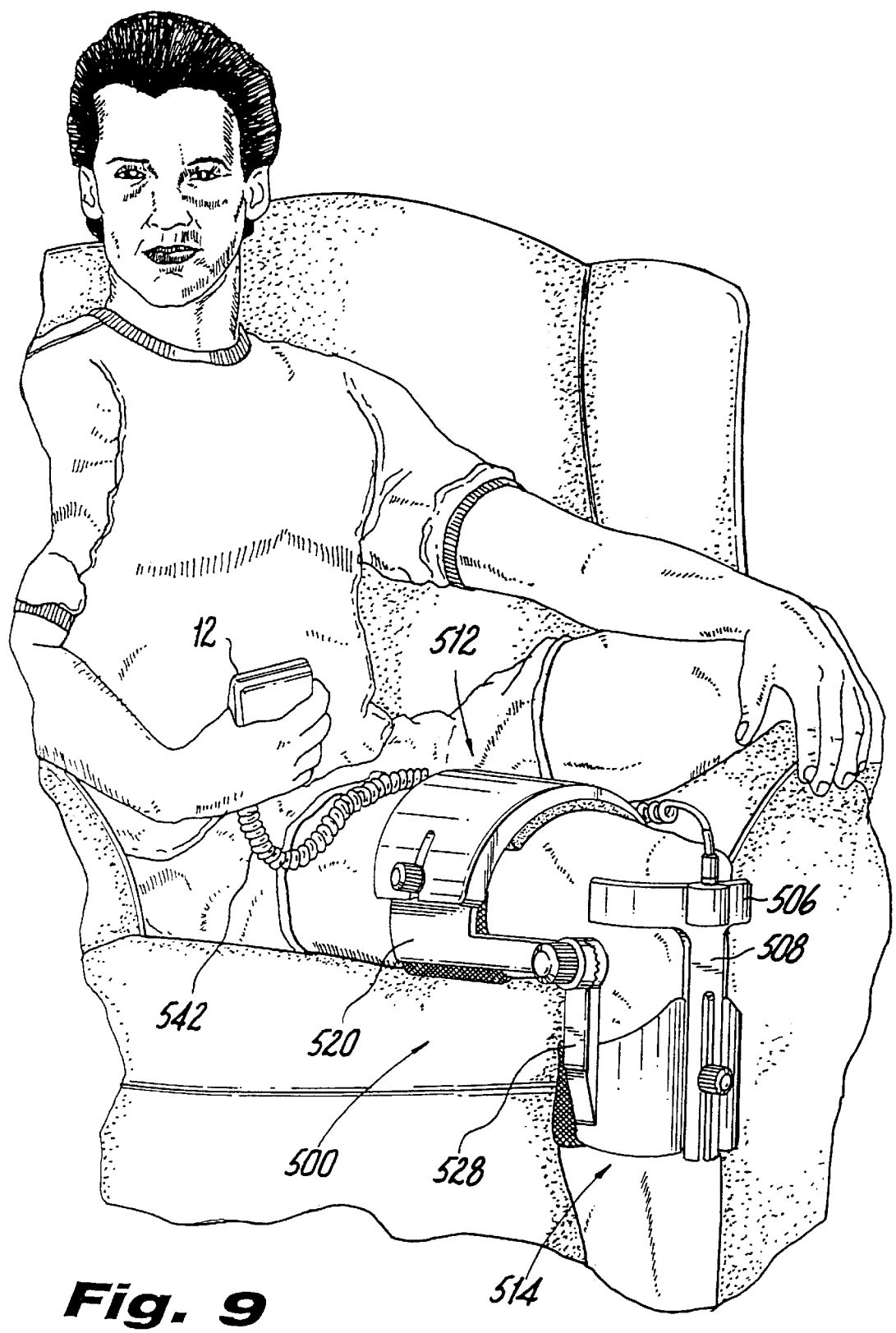
FIG. 9 is a perspective view of a fifth embodiment of the portable ultrasonic treatment apparatus, illustrating a main operating unit or controller and a placement module for treating osteochondral injuries within the knee region.
Figure 10A:
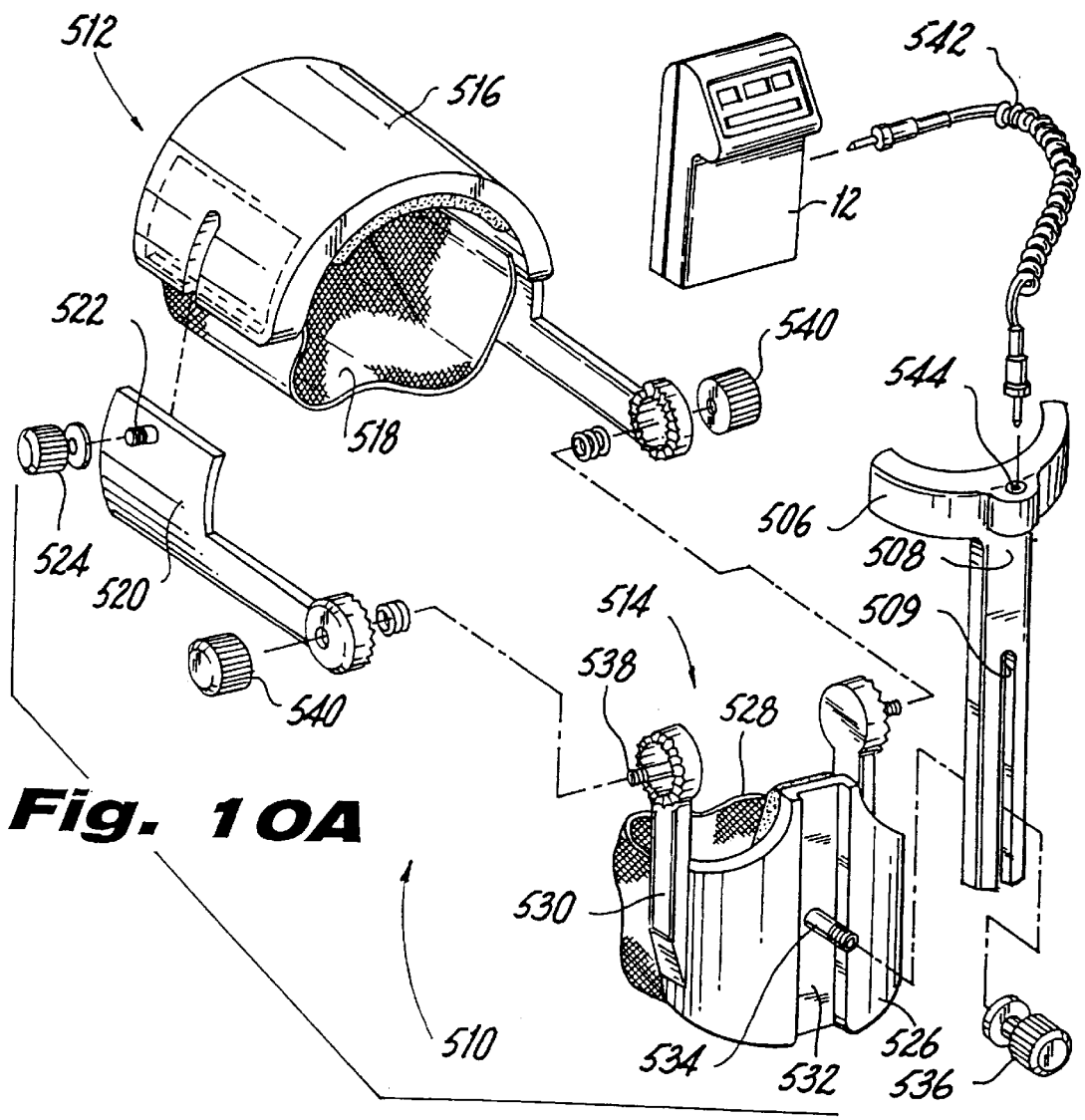
FIG. 10A is an exploded view of the portable ultrasonic treatment apparatus illustrated by FIG. 9.
Figure 10B:
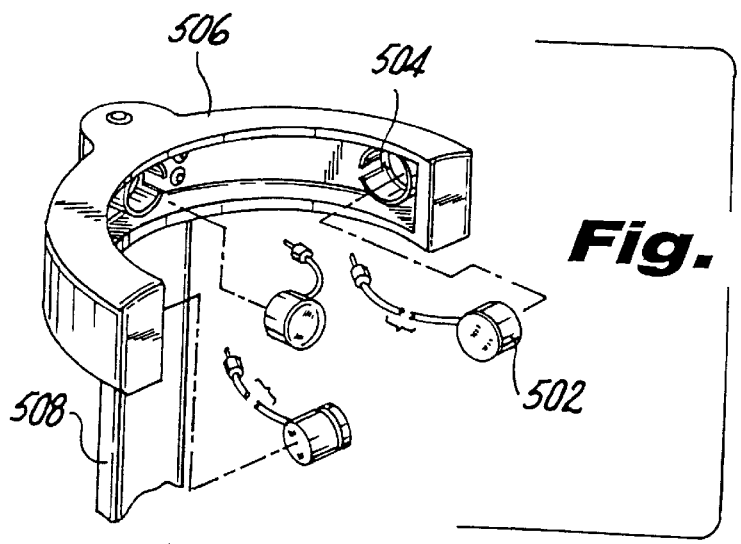
FIG. 10B is a perspective view of a support member of the portable ultrasonic treatment apparatus illustrated by FIG. 9.

A fifth embodiment of the portable ultrasonic treatment apparatus of the present invention which is primarily suitable for the treatment of cartilage and/or osteochondral injuries and/or defects is illustrated by FIGS. 9–10B. In this embodiment, the apparatus 500 includes a MOU 12 and three ultrasonic transducer assemblies 502 positioned within pockets 504 on an inner surface of a concave plate 506 as shown by FIG. 10B. The concave plate 506 is positioned at one end of a vertical bar 508 having a slot 509 at a lower portion. The apparatus 500 further includes a locking support module 510 having a thigh support 512 and a leg support 514.

As shown by the exploded view of FIG. 10A, the thigh support 512 includes a thigh support plate 516, a securing band 518, and two horizontal locking extensions 520 affixed to the thigh support plate 516 by screws 522 and thumb screws 524. The leg support 514 includes a leg support plate 526, a securing band 528, and two vertical locking extensions 530 affixed to the leg support plate 526. The vertical bar 508 is configured to mount within a channel 532 on the leg support 514. The vertical bar 508 is secured to the channel 532 by screw 534 and thumb screw 536. The vertical bar 508 can be moved vertically along the channel 532 by unthreading the thumb screw 536 to accommodate various patients.

The thigh support 512 and the leg support 514 are locked to each other by locking the horizontal locking extensions 520 and the vertical locking extensions 530 by screws 538 and thumb screws 540 to prevent the patient from moving the thigh with respect to the leg during treatment and to ensure that the transducer assemblies 502 remain fixed in their proper positions. The transducer assemblies 502 are connected via a cable 542 which is plugged in to hole 544 to the MOU 12 which contains circuitry for exciting the ultrasonic transducer assemblies 502. It is contemplated that during treatment an ultrasonic conducting gel is positioned between the transducers 502 mounted in concave plate 506 and the patient's body to prevent attenuation of the ultrasonic waves.

Figure 11:
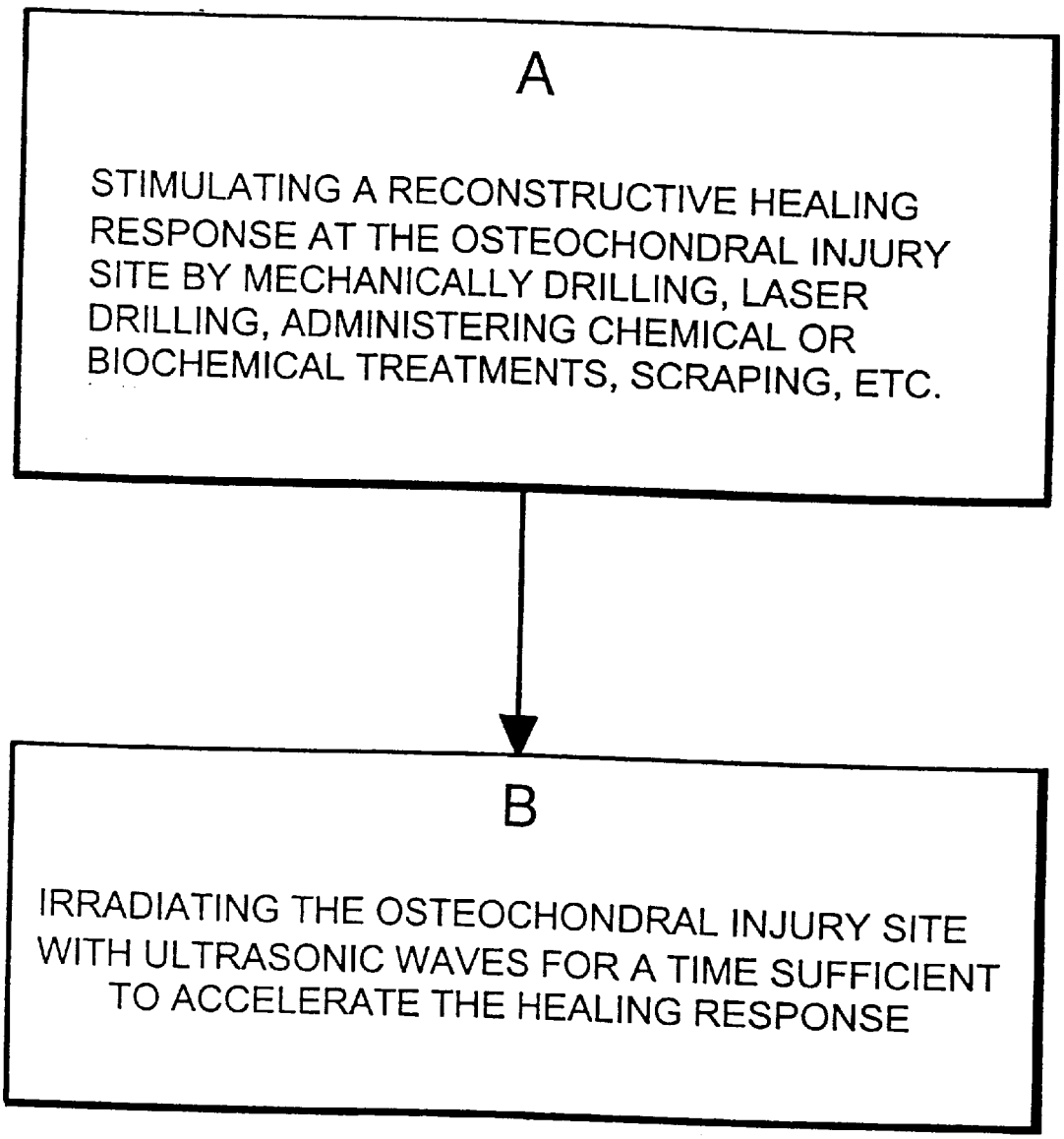
FIG. 11 is a flow-chart depicting the steps for stimulating a healing response at the site of an osteochondral injury according to the present invention.

A method for treating a cartilage and/or osteochondral injury and/or defect is depicted by the flow-chart of FIG. 11. The method entails stimulating blood flow to induce a biological reconstructive healing response of the underlying area at the cartilage and/or osteochondral injury site (step A), and irradiating the cartilage and/or osteochondral injury site with ultrasonic waves for a time sufficient to accelerate the healing response (step B). Step A entails mechanically drilling, induced fracture, laser drilling, administering chemical or biochemical treatments, scraping the injury site to stimulate the growth of cartilaginous tissue. Step B preferably entails propagating a primary directional lobe of acoustic energy in body tissue and/or fluids about a central or longitudinal axis, and this primary directional lobe is concentrically surrounded by primary shearwave lobes of acoustic energy. The carrier frequency is sufficiently elevated to establish a standing-wave condition in one or more spaces between confronting surfaces adjacent or at the cartilage and/or osteochondral injury site, as long as the space is dimensionally characterized by at least a quarter-wavelength at the carrier frequency, thereby enabling demodulation of the carrier frequency. Within a matter of days, healing proceeds at an accelerated pace in the environment of such demodulation, with resultant cartilage development in reduction of the space; but the pattern of carrier wave propagation in body tissue and/or fluids surrounding the central axis of acoustic propagation is rich in therapeutically beneficial shear waves of acoustic energy.

It is also contemplated to use the present method in conjunction with the transplantation of autologous cultured chondrocytes to the injury site to increase the healing time.

Figure 12A:
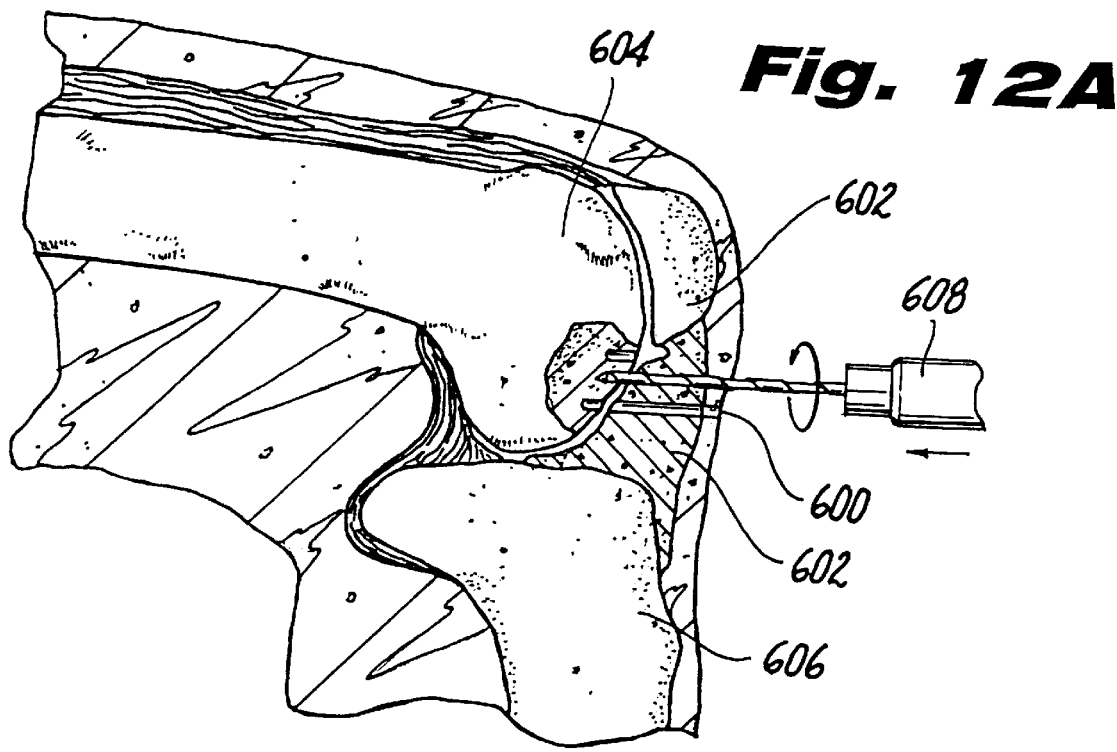
FIG. 12A is a perspective view showing the drilling of channels within the joint walls of the femur and tibia.
Figure 12B:
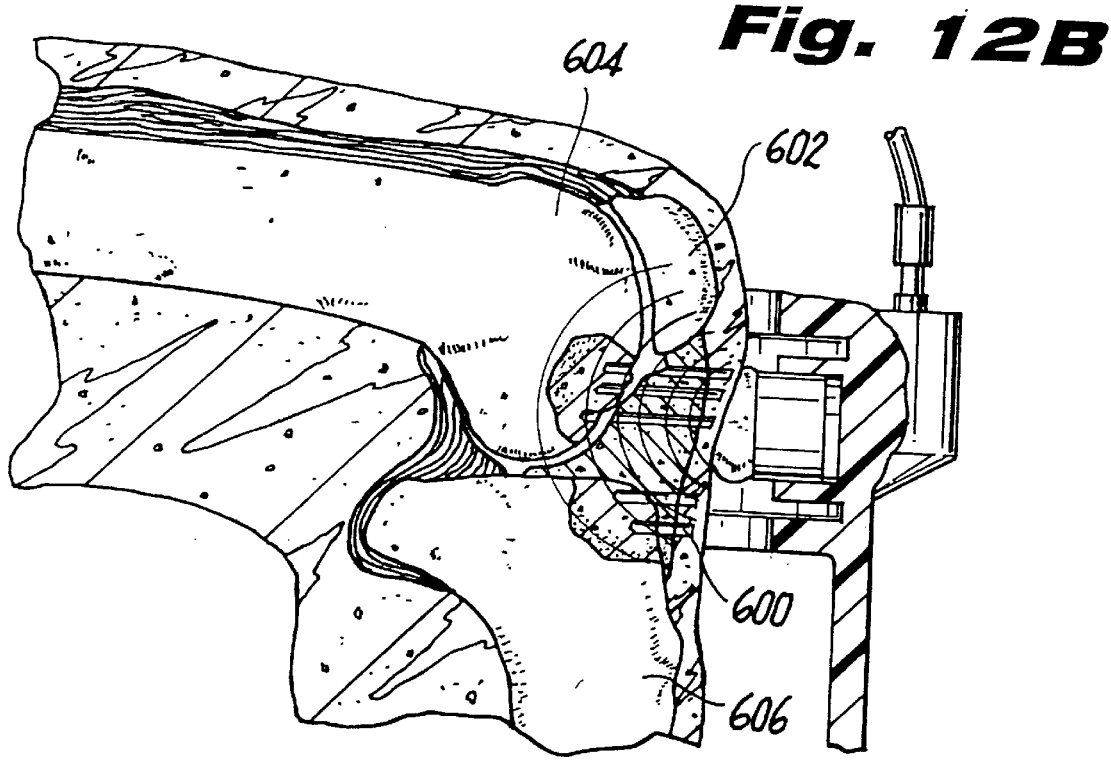
FIG. 12B is a cross-sectional view showing ultrasonic waves "bouncing off" the channels within the joint walls of the femur and tibia.

With reference to FIGS. 12A and 12B, there are illustrated steps A and B, respectively. FIG. 12A is a perspective view showing the drilling of channels 600 within the defect using a drill 608 to stimulate blood flow and induce the biological reconstructive healing response of the underlying area at the cartilage and/or osteochondral injury site. FIG. 12B is a cross-sectional view showing the ultrasonic waves "bouncing off" the channels 600 within the joint walls 602 of the femur 604 and tibia 606 for a time sufficient to accelerate the healing response.

FIGS. 13A–19D are photomicrographs illustrating the postoperative appearance of cartilage and/or osteochondral defects created at the patellar groove region of rabbits according to studies (EXI095-01R and EXI096-01R) conducted to demonstrate that daily ultrasound therapy accelerated cartilage and/or osteochondral defect healing as early as four weeks in both gross and histologic analysis. Defects treated with ultrasound demonstrated more hyaline cartilage properties compared to nontreated sites at four, eight, and twelve weeks postoperative. In addition, greater subchondral bone restoration was also noted.

The second study, EXI096-01R, confirmed the results of the initial study, EXI095-01R, and added longer term (12 weeks) analysis. The four week postoperative ultrasound treated defects received higher gross and histologic scores compared to the nontreated defects, indicating accelerated tissue regeneration and higher levels of proteoglycan formation and cartilage like morphology and greater integration of the repair cartilage with the surrounding host cartilage. The mean gross grade for the ultrasound treated defects was 6.92/8 versus 4.83/8 for the nontreated defects at four weeks. The mean histologic grade for the ultrasound defects was 15.11/24 versus 9.28/24 for the nontreated defects at four weeks. At eight weeks postoperative, differences were more subtle both grossly and histologically between treated and nontreated defects. The mean gross grade for the ultrasound defects was 7.50/8 compared to 6.33/8 for the nontreated defects at eight weeks. The mean histologic grade for the ultrasound defects was 15.83/24 compared to 13.60/24 for the nontreated defects at eight weeks. However, at twelve weeks postoperative, dramatic differences were observed grossly between the treated and nontreated defects (7.17/8 gross grade for ultrasound defects versus 5.50/8 for nontreated defects). This may represent the initial degeneration of the inferior cartilage produced in the nontreated defects. The mean histologic grade for the ultrasound treated defects was 19.06/24. The mean grade for the nontreated defects was 15.06/24.

Overall, ultrasound treated sites demonstrated earlier and greater amounts of cartilage and subchondral bone regeneration. With time ultrasound sites demonstrated more extensive subchondral bone regeneration, less degeneration of adjacent cartilage, and greater chondral layer thickness and a greater amount of integration of the repair cartilage with surrounding host cartilage. These characteristics indicate a better quality of repair cartilage, that may be better able to withstand loading and degeneration over time.

A total of 18 male New Zealand White rabbits weighing five to nine pounds at acquisition were utilized. Specific attention was paid in selecting animals of uniform size to limit variability in loading the osteochondral defects. Bilateral 3 mm diameter by 5 mm deep osteochondral defects were created surgically in the patellar groove of each femur. Daily 20 minute ultrasound therapy was applied to the right knee defects only until sacrifice. The left defects were not treated. In an initial pilot study of six animals (EXI095-01R) three were sacrificed at four weeks postoperative and three were sacrificed at eight weeks postoperative. Each defect was evaluated grossly and histologically for the quality and extent of cartilage regeneration. Based on the four and eight week gross and four week histologic results, a second similar study was undertaken (EXI096-01R) consisting of 12 rabbits. A gross pathologic examination was made of all vital organs and systems. A summary of the surgery and treatment schedule for both studies appears in Table 1.

TABLE 1

Treatment Schedule (EXI095-01R and EXI096-01R)

| Animal Number | Right Knee Treatment | Left Knee Treatment | Surgery Date | Duration |
|---|---|---|---|---|
| EXI095-01R: | | | | |
| G200 | 20 minute daily | none | May 16, 1996 | 4 weeks |
| G203 | 20 minute daily | none | May 16, 1996 | 4 weeks |
| G217 | 20 minute daily | none | May 16, 1996 | 4 weeks |
| G198 | 20 minute daily | none | May 16, 1996 | 8 weeks |
| G201 | 20 minute daily | none | May 16, 1996 | 8 weeks |
| G202 | 20 minute daily | none | May 16, 1996 | 8 weeks |
| EXI096-01R: | | | | |
| H155 | 20 minute daily | none | July 26, 1996 | 4 weeks |
| H156 | 20 minute daily | none | July 26, 1996 | 4 weeks |
| H160 | 20 minute daily | none | July 26, 1996 | 4 weeks |
| H152 | 20 minute daily | none | July 26, 1996 | 8 weeks |
| H153 | 20 minute daily | none | July 26, 1996 | 8 weeks |
| H162 | 20 minute daily | none | July 26, 1996 | 8 weeks |
| H154 | 20 minute daily | none | July 26, 1996 | 12 weeks |
| H157 | 20 minute daily | none | July 26, 1996 | 12 weeks |
| H161 | 20 minute daily | none | July 26, 1996 | 12 weeks |
| H163 | 20 minute daily | none | July 26, 1996 | 12 weeks |
| H164 | 20 minute daily | none | July 26, 1996 | 12 weeks |
| H165 | 20 minute daily | none | July 26, 1996 | 12 weeks |

The right knees received 20 minute daily ultrasound therapy with the Sonic Accelerated Fracture Healing (SAFHS) device six days weekly beginning on postoperative day four. The left knees received no treatment. SAFHS units were randomly chosen each day for treatment. Due to the large number of animals in the study EXI096-01R, some devices were used twice each day on two different animals. Animals were sedated by intramuscular injection of Ketaset and Rompun (83 mg/ml Ketamine and 17 mg/ml xylazine) at the dosage of 0.3 mg/kg body weight in order to administer the therapy. This dosage is approximately one half the anesthetic dosage intended to provide sedation only. The ultrasound transducer was placed on the distal femur at the lateral condyle with ample ultrasound coupling gel. The sites were periodically shaved to ensure contact between the transducer, coupling gel and skin.

The SAFHS device is a noninvasive FDA approved external device indicated for the accelerated healing of fresh fractures. SAFHS delivers a low level acoustic pressure wave signal with an intensity of 30 milliwatts per square centimeter (equivalent to the intensity used for diagnostic ultrasound) to the skin at the fracture site for twenty minutes daily.

Figure 13A:
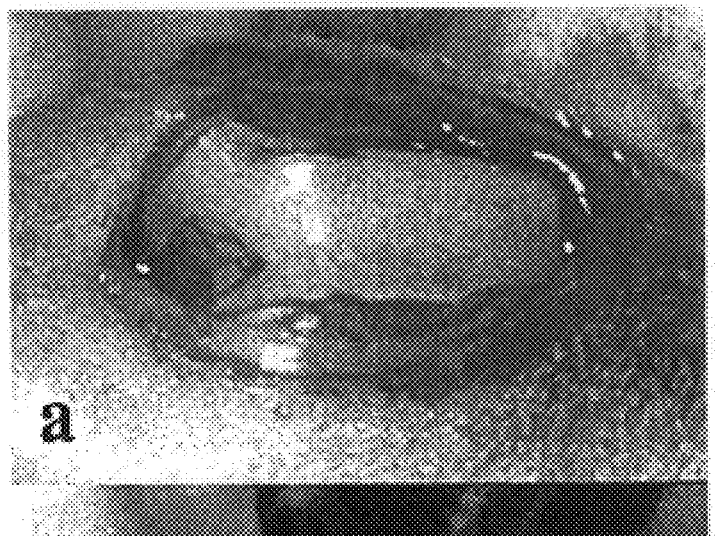
FIGS. 13A–19D are photomicrographs illustrating the postoperative appearance of cartilage and/or osteochondral defects created at the patellar groove region of rabbits according to a study conducted to demonstrate that daily ultrasound therapy accelerated cartilage and/or osteochondral defect healing as early as four weeks in both gross and histologic analysis.
Figure 13B:
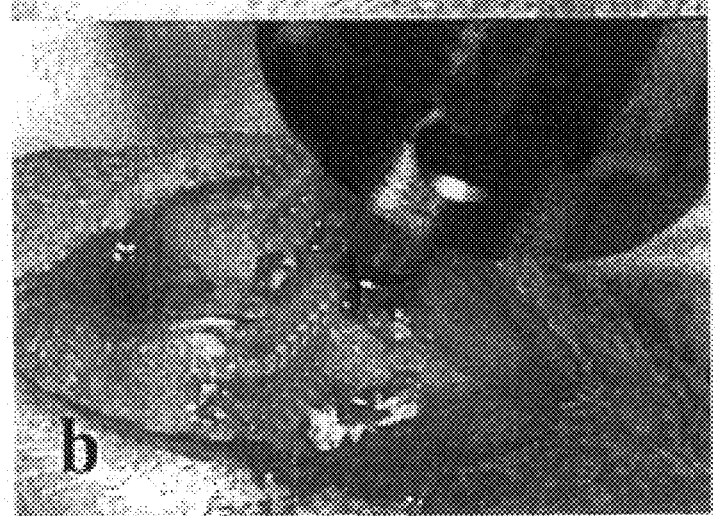
Figure 13C:

Using standard aseptic techniques, surgery was performed under halothane gas anesthesia and was monitored by electrocardiogram and heart rate monitors. Anesthesia was administered by intramuscular injection of Ketaset and Rompun (83 mg/ml Ketamine and 17 mg/ml xylazine) at the dosage of 0.6 mg/kg body weight. Both hind limbs were prepped and draped in sterile fashion. The defect in the knee joint was made though a median parapatellar incision. The connective tissue securing the patella was partially released to dislocate the patella and expose the media] femoral condyle and patellar groove (FIG. 13A). Using a drill bit, a 3 mm diameter by 5 mm deep osteochondral defect in the patellar sulcus of the femur was created (FIG. 13B). After irrigation with saline, the joint was closed in layers (FIG. 13C). Routine anterior-posterior radiographs were taken after surgery to insure proper defect location.

Butorphanol tartrate (0.2 mg/kg body weight) was administered subcutaneously as required. Animals were administered intramuscular antibiotics for four days postsurgery. Animals were kept in recovery cages postoperatively until fully conscious and demonstrated weight bearing, after which they were transferred to standard cages and allowed unrestricted motion. Halo collars were utilized as needed to prevent the animal from removing sutures.

Osteochondral healing was evaluated grossly and histologically. Radiographs were utilized as necessary to evaluate healing. Animals were observed daily by qualified personnel for any signs of ill health or adverse reaction to the experimental procedures.

Both right and left distal femurs were harvested en bloc, carefully labeled, and kept in cool saline until gross grading and microphotography was completed. The specimens were then placed in formalin based fixative and labeled with all necessary identifications. A gross pathological exam of vital organs was conducted by the in-house veterinarian. Microscopic pathologic examination was performed on any tissues determined to be grossly abnormal.

Each harvested defect knee was graded for gross appearance based upon the scheme of Moran et. al. (*The Journal of Bone and Joint Surgery,* 74-B, 659–667, 1992) by an observer blinded to the treatment group. This analysis apportions points based upon the formation of intra-articular adhesions, restoration of articular surface, erosion and appearance of the cartilage. A total of eight points is the best possible grade (Table 2.)

TABLE 2

| Gross Grading Scale | |
|---|---|
| | Grades |
| Intra-articular adhesions | |
| None = | 2 |
| Minimal/fine loose fibrous tissue = | 1 |
| Major/dense fibrous tissue = | 0 |
| Restoration of articular surface | |
| Complete = | 2 |
| Partial = | 1 |
| None = | 0 |
| Erosion of cartilage | |
| None = | 2 |
| Defect site/site border = | 1 |
| Defect site and adjacent normal cartilage = | 0 |
| Appearance of cartilage | |
| Translucent = | 2 |
| Opaque = | 1 |
| Discolored or irregular = | 0 |
| TOTAL SCORE | 8 possible points |

All specimens were prepared for histologic evaluation. The individual specimens were fixed by immersion in either 10% formalin solution or 4% paraformaldehyde solution. Following fixation, the specimens were slowly decalcified in EDTA. The defect area was bisected across the diameter of the defect. The resulting halves and surrounding tissue were embedded in paraffin and sectioned across the defect site. Three sections, 5–7 um thick, from three levels were cut from each block. Level 1 was closest to the defect center. Level 3 was closest to the defect perimeter and level 2 was centered between levels 1 and 3. Three sections from each level were stained with hematoxylin and eosin, Goldner's trichrome, and safranin-O and Fast Green stains (to indicate glycosaminoglycan content in the matrix).

Decalcified histologic sections were evaluated by an observer blinded to treatment group. Sections were graded base upon the scheme of Moran et. al. which apportion points based upon the nature of the repair cartilage, structural characteristics, and cellular changes (Table 3.)

TABLE 3

| Histology Grading Scale | |
|---|---|
| NATURE OF THE PREDOMINANT TISSUE: | |
| Cellular morphology | |
| Hyaline articular cartilage = | 4 |
| Incompletely differentiated = | 2 |
| Fibrous tissue or bone = | 0 |
| Safranin-O staining of the matrix | |
| Normal/near normal = | 3 |
| Moderate = | 2 |
| Slight = | 1 |
| None = | 0 |
| STRUCTURAL CHARACTERISTICS: | |
| Surface regularity | |
| Smooth/intact = | 3 |
| Superficial horizontal lamination = | 2 |
| Fissures, 25–100% of thickness = | 1 |
| Severe disruption, fibrillation = | 0 |
| Structural integrity | |
| Normal = | 2 |
| Slight disruption, including cysts = | 1 |
| Severe disintegration = | 0 |
| Thickness | |
| 100% of normal cartilage thickness = | 2 |
| 50–100% = | 1 |
| 0–50% = | 0 |
| Bonding to the adjacent cartilage | |
| Bonded at both ends of the defect = | 2 |
| Bonded at one end or partially bonded at both ends = | 1 |
| Not bonded = | 0 |
| FREEDOM FROM CELLULAR CHANGES OF DEGENERATION: | |
| Hypocellularity | |
| None = | 3 |
| Slight = | 2 |
| Moderate = | 1 |
| Severe = | 0 |
| Chondrocyte clustering | |
| None = | 2 |
| <25% of cells = | 1 |
| >25% of cells = | 0 |
| Freedom from degenerative changes in adjacent cartilage | |
| Normal cellularity, no clusters, normal staining = | 3 |
| Normal cellularity, mild clusters, moderate staining = | 2 |
| Mild or moderate hypocellularity, slight staining = | 1 |
| Severe hypocellularity, poor or no staining = | 0 |

Immunohistochemical staining of cartilage sections from twelve week ultrasound treated and nontreated defects was performed to identify Type I and Type II collagen. Goat antihuman polyclonals obtained from Southern Biotechnology, Inc. were used. Immunohistochemical staining identifies the critical components of articular cartilage necessary for correct regeneration and maintenance of the tissue phenotype. In addition, the presence of other tissues reflective of inappropriate tissue formation is identified. In hyaline articular cartilage Type II collagen should be localized only in the cartilage layer above the subchondral bone. Staining for Type I collagen should be restricted to the subchondral bone region.

All surgeries were uneventful with no postoperative complications. Pathologic examination of internal organs demonstrated no adverse response to the daily ultrasound treatment or experimental procedures.

A summary of the gross evaluation grades from studies EXI095-01R and EXI096-01R appears in Table 4. FIGS. 2 through 4 demonstrate the typical gross appearance of the treated and nontreated sites at four, eight, and twelve weeks postoperative.

TABLE 4

Mean Gross Evaluation Grade ± standard deviation (n = 6)

|  | NONTREATED | ULTRASOUND |
|---|---|---|
| 4 WEEKS | 4.83 ± 1.72 | 6.92 ± 1.02 |
| 8 WEEKS | 6.33 ± 0.82 | 7.50 ± 0.45 |
| 12 WEEKS | 5.50 ± 1.22 | 7.17 ± 0.98 |

Figure 14:
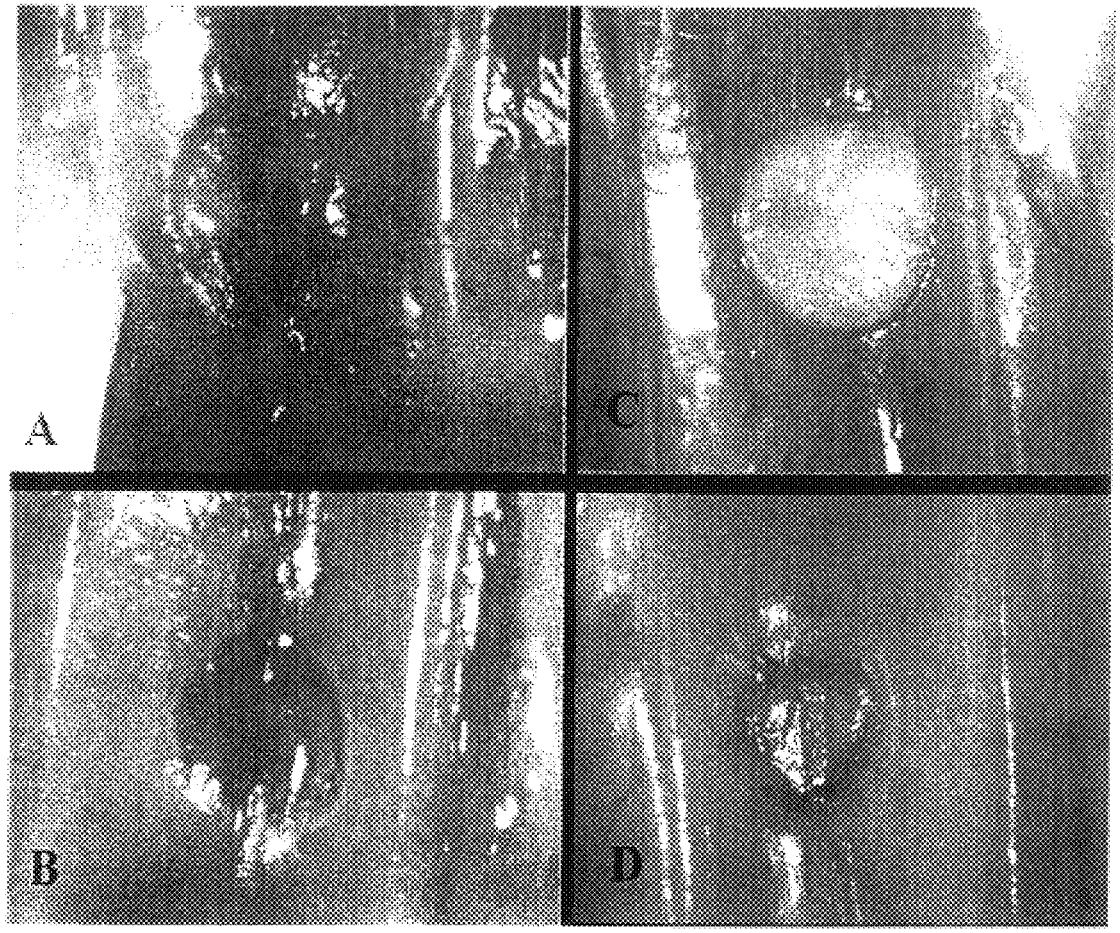
Figure 15:
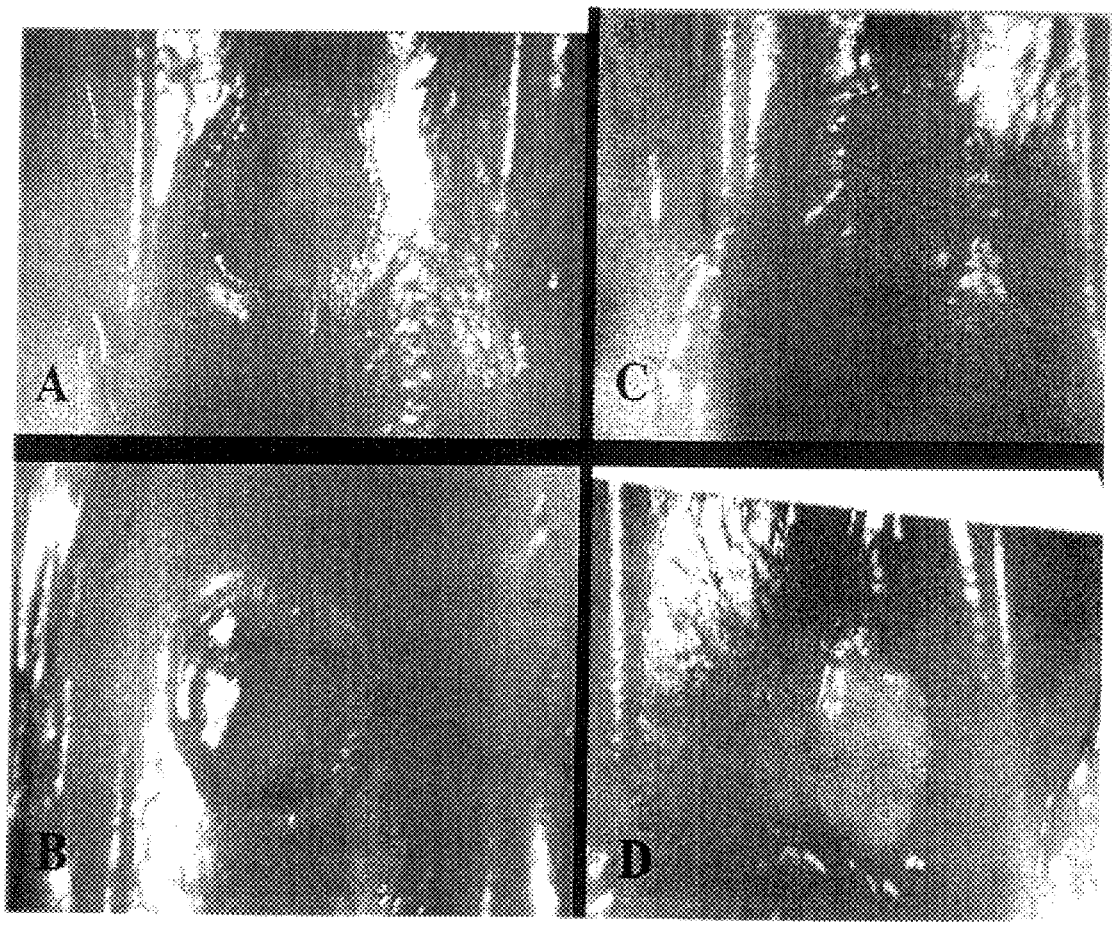
Figure 16:
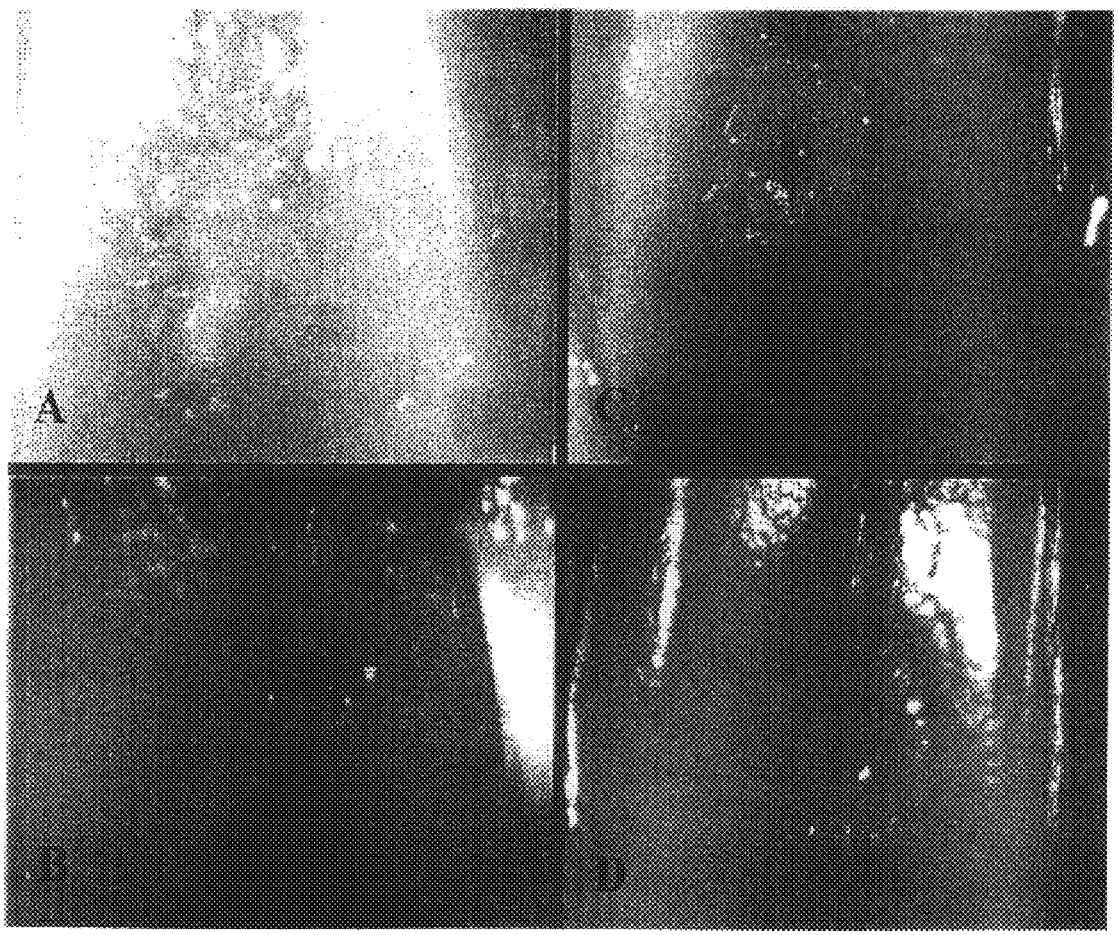
Figure 17A:
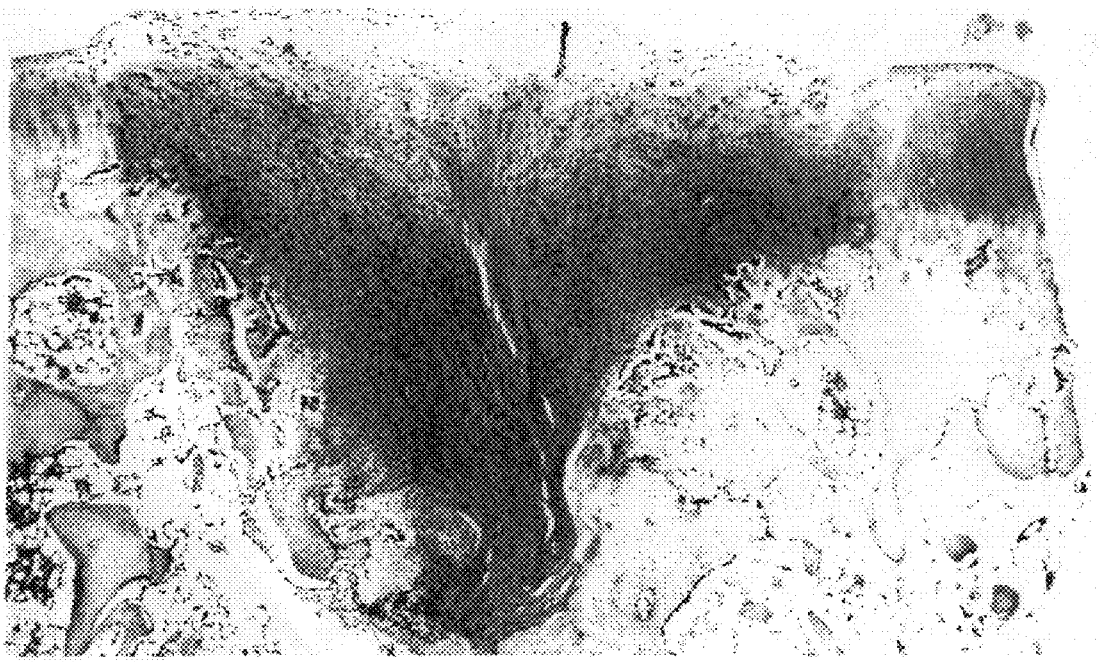
Figure 17B:
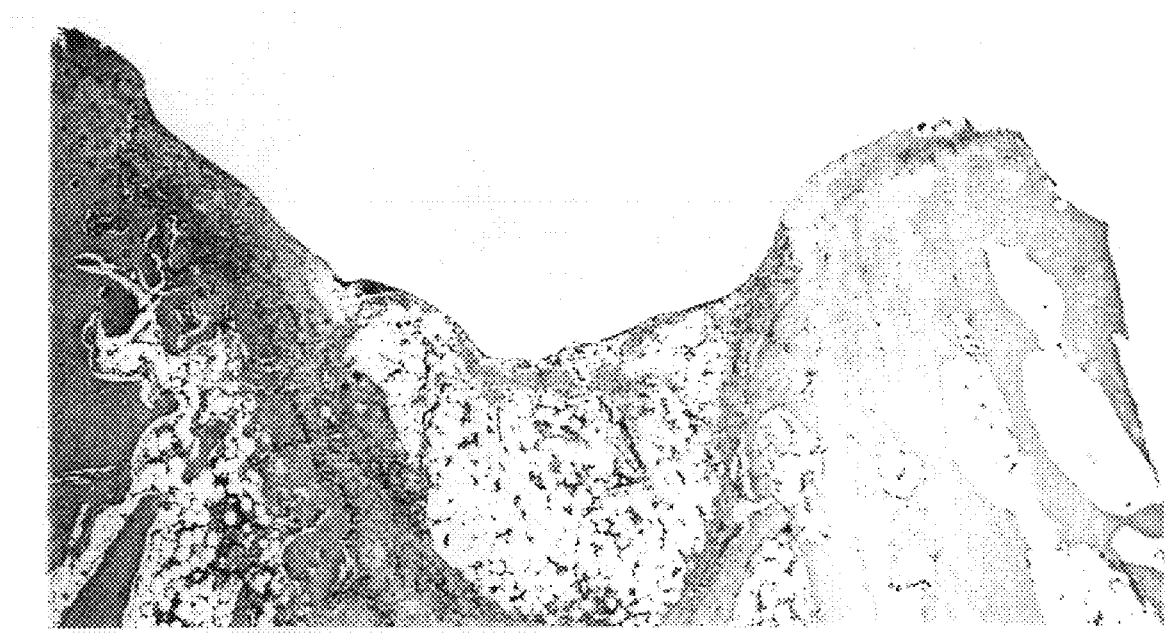
Figure 17C:
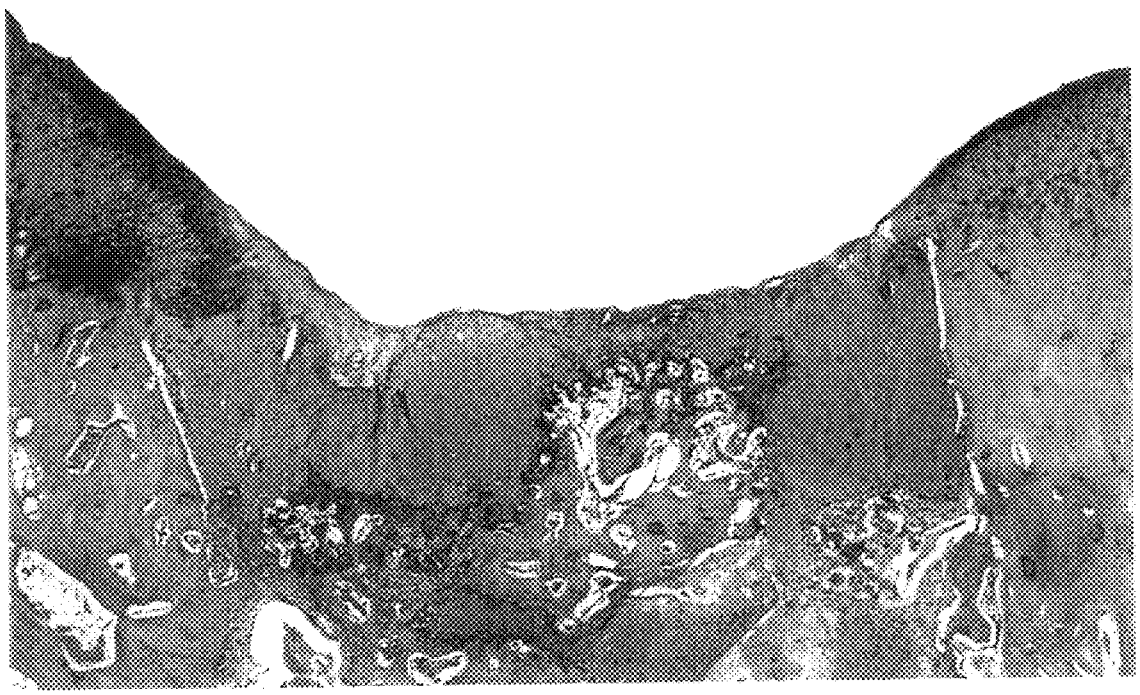
Figure 17D:
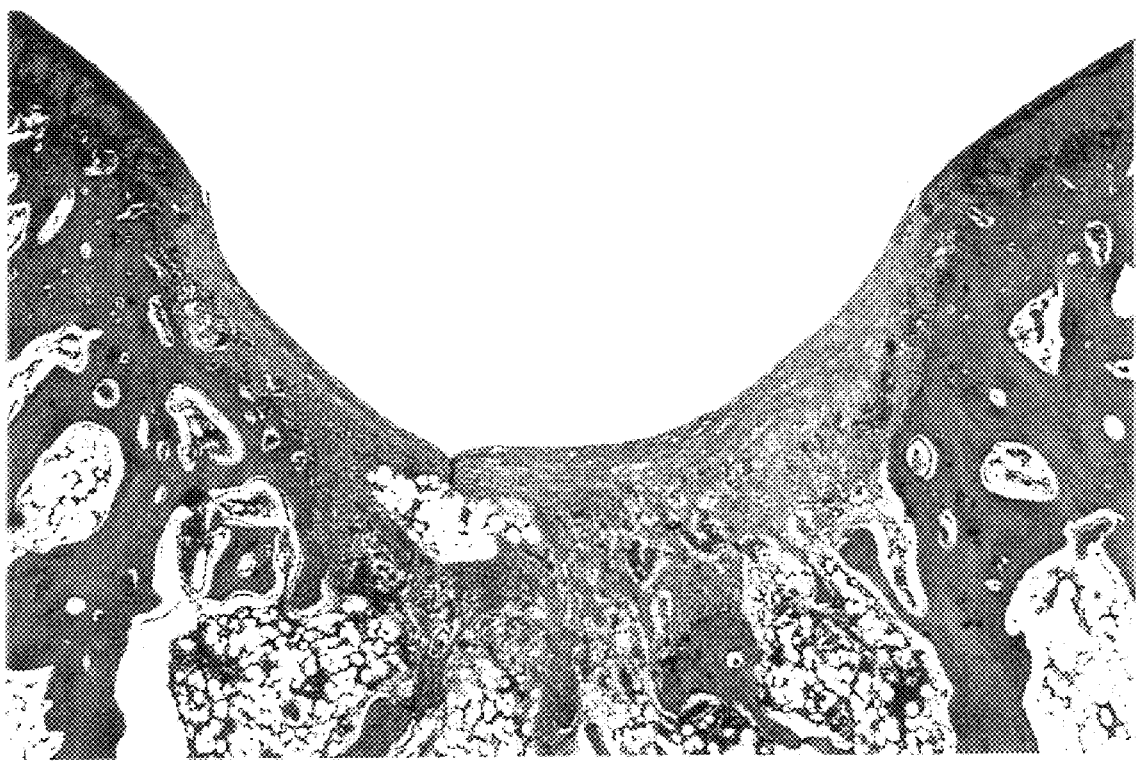
Figure 18A:
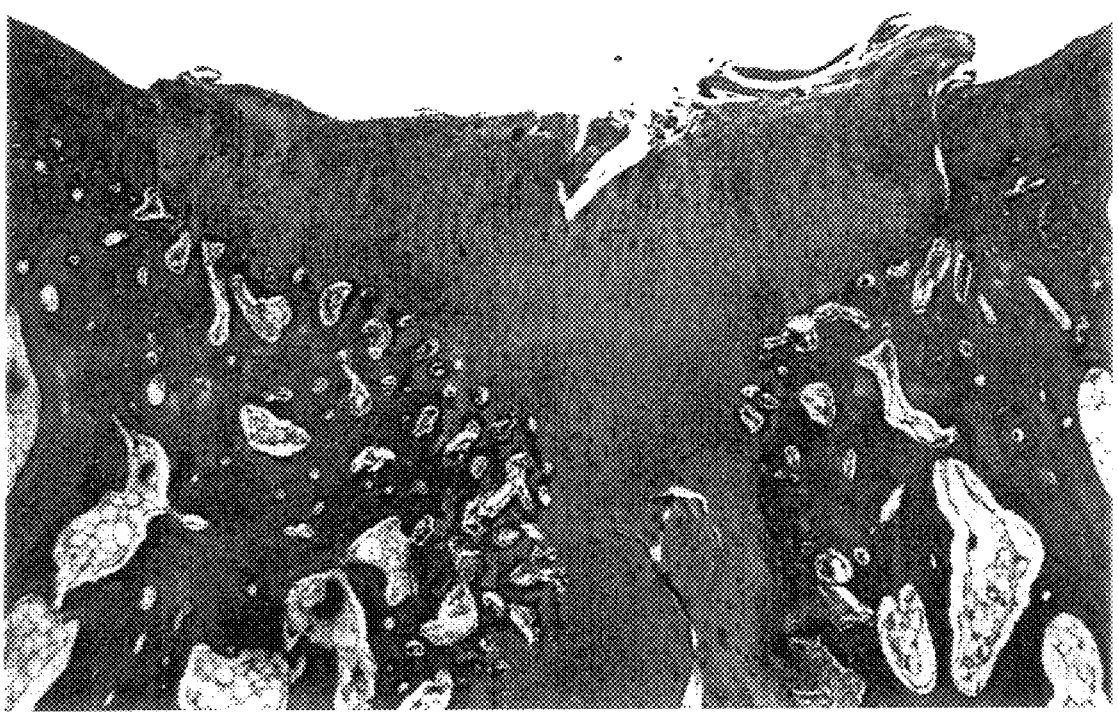
Figure 18B:
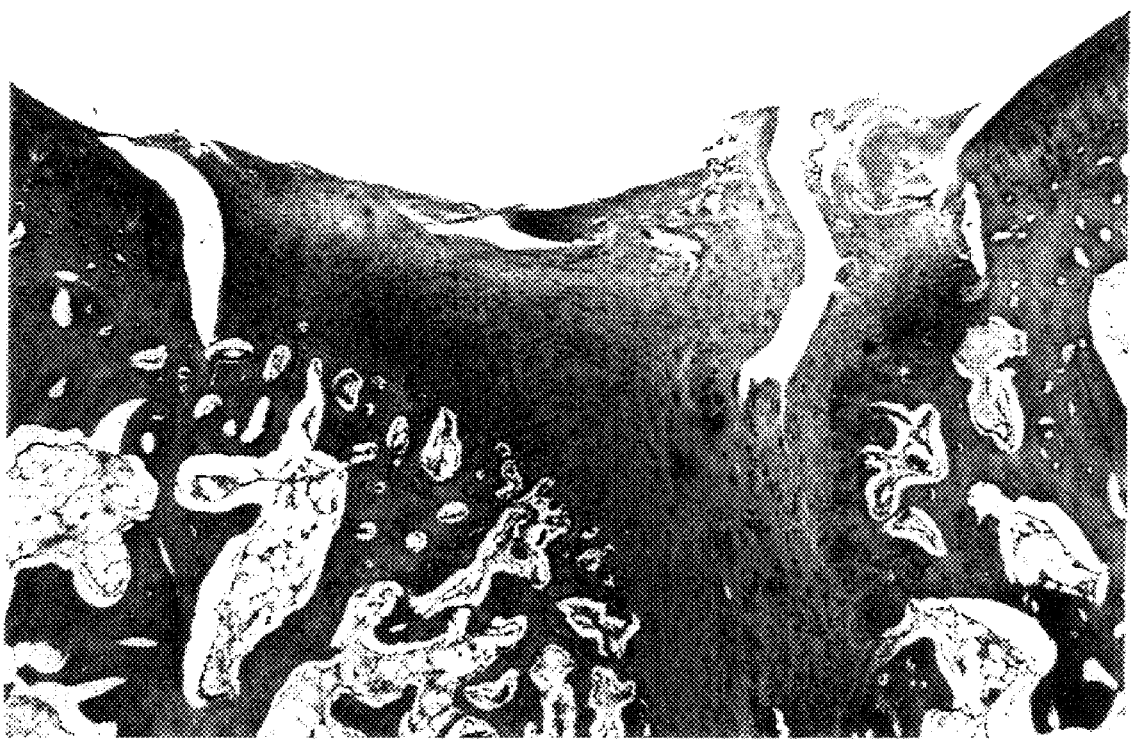
Figure 18C:
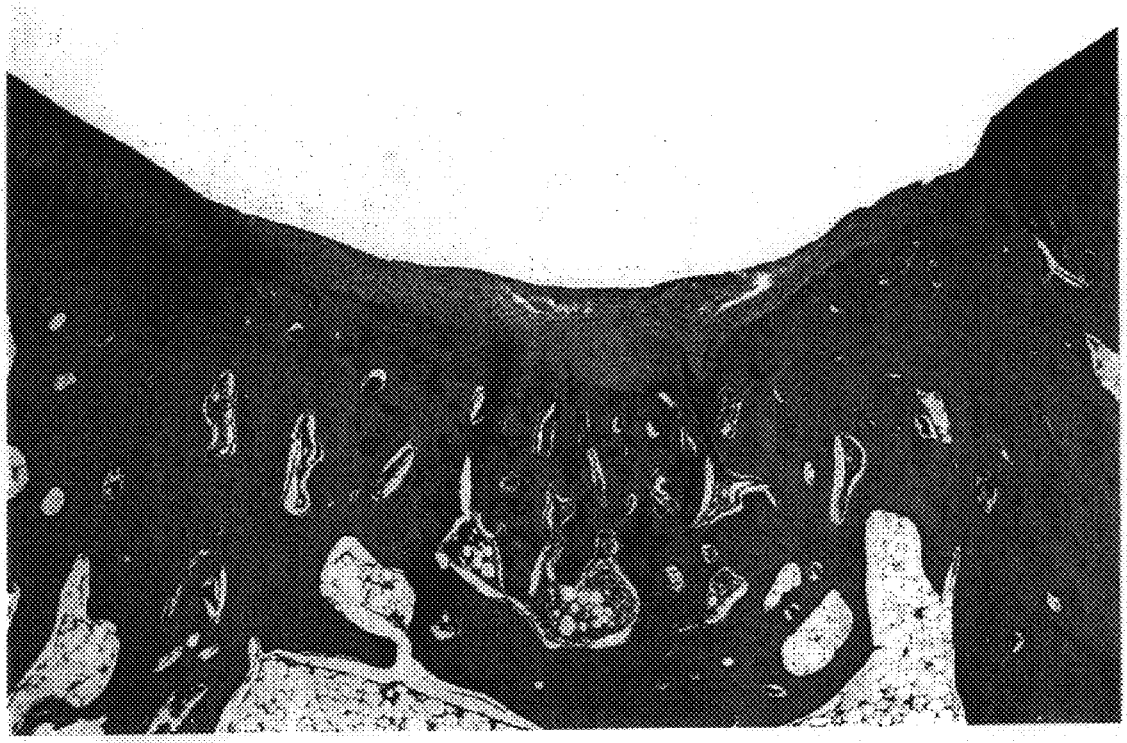
Figure 18D:
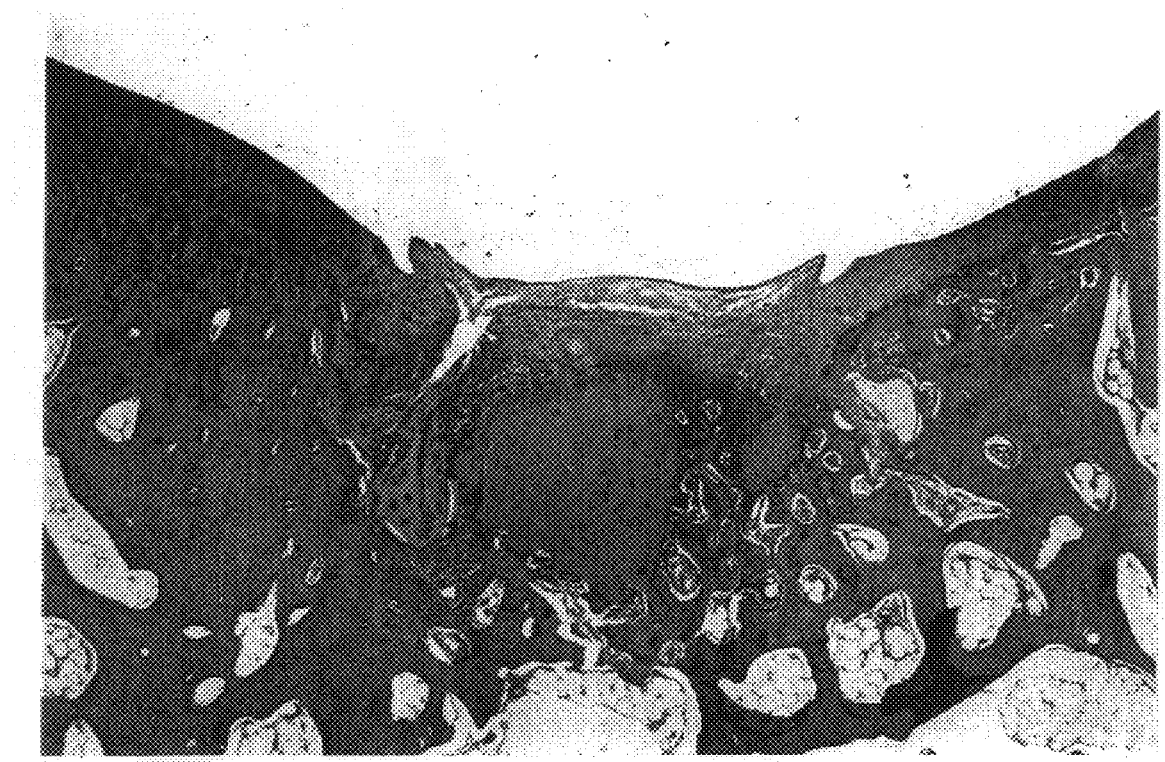
Figure 19A:
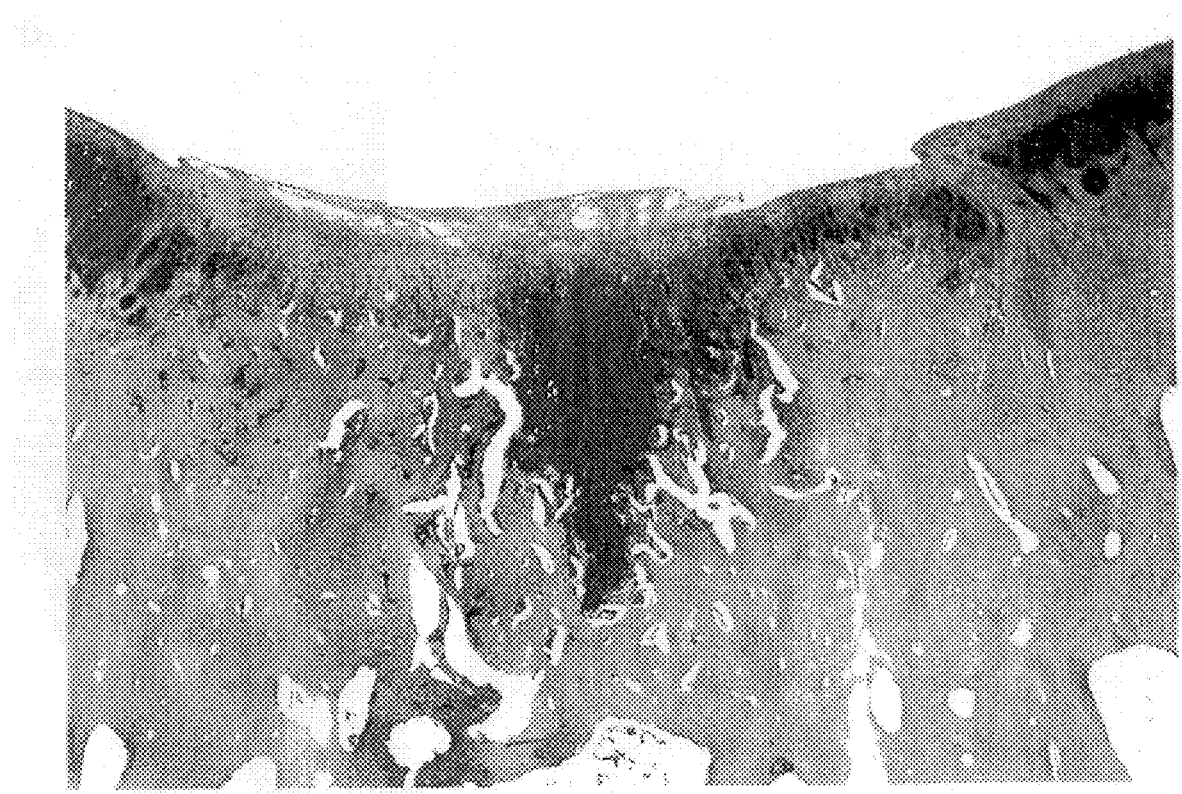
Figure 19B:
Figure 19C:
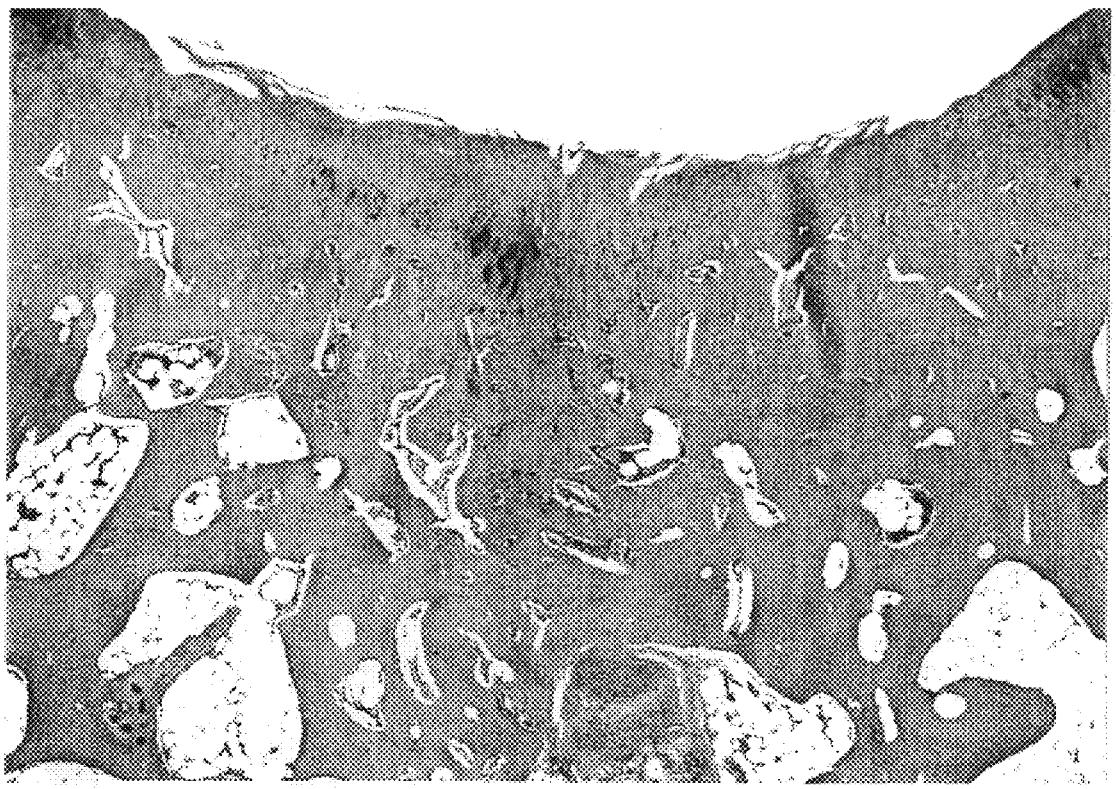
Figure 19D:
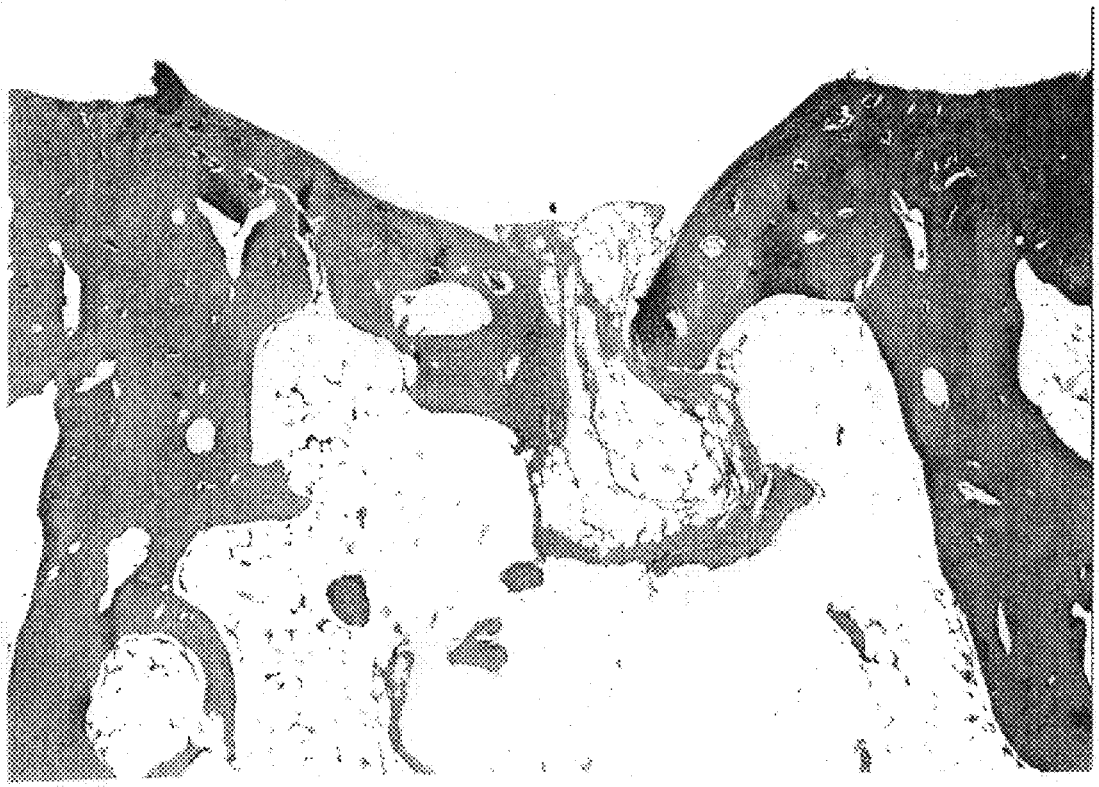

At four weeks postoperative the ultrasound treated defects demonstrated more complete and uniform covering of the defect, although typically the new cartilage had an opaque appearance. Incompletely covered lesions were present at the center of many of the nontreated sites and the tissue regenerated was irregular in color (FIG. 14). By eight weeks both the ultrasound and nontreated defects were covered uniformly with new tissue. The ultrasound treated defects demonstrated less erosion of the new cartilage and surrounding intact cartilage (FIG. 15). At twelve weeks postoperative the defect borders in the ultrasound treated defects were difficult to appreciate and the new cartilage had the appearance of the adjacent tissue (FIG. 16) and it was well integrated with the adjacent host cartilage. New cartilage had a more transparent appearance compared to the nontreated defects and clearly demonstrated significantly less erosion of the adjacent and newly formed cartilage.

A summary of the mean histologic grades from studies EXI095-01R and EXI096-01R appears in Table 5. One half of each twelve week specimen has been submitted for tissue typing analysis aimed at identifying the collagen type and percent tissue composition.

Intense safranin-O staining of the matrix, extensive chondroblast activity, and earlier subchondral bone formation in the ultrasound treated defects was in sharp contrast with the lack of activity and chondroblast phenotype present in the nontreated defects. Early degenerative changes of the nontreated defects was also evident.

At eight weeks the histologic results were similar to the gross results. Generally, safranin-O staining was not as intense at eight weeks postoperative in both the ultrasound treated and nontreated defects. However, subchondral bone regeneration was complete in the ultrasound treated sites and the repair cartilage showed less signs of degenerative changes. The nontreated sites showed less subchondral bone regeneration and organization of the repair tissue.

Again at twelve weeks the ultrasound treated site had greater mean histologic scores than the nontreated defects. In most cases, subchondral bone regeneration was complete. However, the chondral layer repair tissue in ultrasound treated sites demonstrated more articular cartilage characteristics than the nontreated sites. The majority of the nontreated sites were covered with superficial layer of maturing fibrous tissue. The intensity of safranin-O stain was slight or not present in the surface repair layer of nontreated defects. Adjacent intact cartilage was hypocellular and in several cases large clusters of greater than 20 chondrocytes were present at the junction between the repair tissue and the host cartilage. Safranin-O staining was more intense in the ultrasound treated sites, however, variations within the repair cartilage of individual defects were observed. Regions of columnar arrangement of chondrocytes, near normal chondral layer thickness and safranin-O staining intensity were present in ultrasound treated defects.

Strong Type II collagen staining of the newly regenerated cartilage layer was found in ultrasound treated defects that showed good repair, whereas nontreated defects sections with poor repair showed less intensive staining or staining of cartilage deep within the defect reflective of inappropriate tissue formation.

TABLE 5

Mean Histologic Grades for the four, eight, and twelve weeks postoperative sites ± standard deviation (sample size) for both EXI095-01R and EXI096-01R.

|  | 4 Weeks Postoperative | | 8 Weeks Postoperative | | 12 Weeks Postoperative | |
|---|---|---|---|---|---|---|
|  | Nontreated | Ultrasound | Nontreated | Ultrasound | Nontreated | Ultrasound |
| Nature of the Predominant Tissue | 1.11 ± 1.02 (18) | 4.06 ± 2.44 (18) | 3.87 ± 1.77 (15) | 3.72 ± 1.81 (18) | 3.50 ± 2.09 (18) | 5.61 ± 1.20 (18) |
| Structural Characteristics | 5.78 ± 1.86 (18) | 6.78 ± 1.29 (18) | 6.27 ± 1.49 (15) | 7.28 ± 1.07 (18) | 6.22 ± 1.99 (18) | 7.17 ± 1.65 (18) |
| Freedom From Cellular Changes of Degeneration | 2.39 ± 1.72 (18) | 4.28 ± 1.67 (18) | 3.47 ± 1.73 (15) | 4.83 ± 1.79 (18) | 5.33 12.52 (18) | 6.28 ± 1.02 (18) |
| TOTAL (out of 24 possible points) | 9.28 ± 3.61 (18) | 15.11 ± 4.80 (18) | 13.60 ± 3.68 (15) | 15.83 ± 2.81 (18) | 15.06 ± 6.30 (18) | 19.06 ± 2.73 (18) |

FIGS. 17, 18, and 19 demonstrate the typical histologic appearance of both treated and nontreated defects at four, eight, and twelve weeks postoperative.

At four weeks postoperative differences between the ultrasound treated and nontreated defects were substantial.

Positive staining for Type I collagen in the regenerated bone showed very little or no localization in the regenerated cartilage layer of the ultrasound treated samples. Presence of Type I collagen in the non-bone areas would be an indication of fibrosis or formation of fibrocartilage.

An additional study, EXI097-01R, was conducted on 66 rabbits which received bilateral osteochondral defects in the femurs according to the study design described above. A summary of the gross grading results from this study pooled with those from studies EXI095-01R and EXI096-01R are presented in "Gross Grading Results" in Table 6.

TABLE 6

Gross Grading Results

| Treatment Group | Evaluation Period | | TOTAL |
|---|---|---|---|
| Abrasion Defects | 4 weeks | Mean | 5.7 |
| 20 mins. ultrasound | | Std. Dev. | 1.0 |
| | | Sample Size | 6 |
| Control | | Mean | 4.8 |
| | | Std. Dev. | 0.8 |
| | | Sample Size | 6 |
| Medial Condyle | 4 weeks | Mean | 4.9 |
| Defects | | Std. Dev. | 1.4 |
| 20 mins. ultrasound | | Sample Size | 6 |
| Control | | Mean | 4.8 |
| | | Std. Dev. | 0.6 |
| | | Sample Size | 6 |
| Patellar Groove | 4 weeks | Mean | 5.5 |
| Defects | | Std. Dev. | 1.0 |
| 20 mins. ultrasound | | Sample Size | 6 |
| Control | | Mean | 5.8 |
| (paired) | | Std. Dev. | 0.3 |
| | | Sample Size | 6 |
| Patellar Groove | 4 weeks | Mean | 6.7 |
| Defects | | Std. Dev. | 1.0 |
| 20 mins. ultrasound | | Sample Size | 6 |
| 5 mins. ultrasound | | Mean | 5.8 |
| | | Std. Dev. | 1.0 |
| | | Sample Size | 6 |
| Patellar Groove | 4 weeks | | |
| Defects | | ONGOING | |
| 20 mins. ultrasound | | | |
| 5 mins. ultrasound | | | |
| Patellar Groove | 4 weeks | | |
| Defects | | ONGOING | |
| 20 mins. ultrasound | | | |
| 10 mins. ultrasound | | | |
| Patellar Groove | 4 weeks | | |
| Defects | | ONGOING | |
| 20 mins. ultrasound | | | |
| 40 mins. ultrasound | | | |
| Patellar Groove | 4 weeks | Mean | 6.6 |
| Defects | | Std. Dev. | 1.0 |
| 20 mins. ultrasound (pooled) | | Sample Size | 18 |
| Control | | Mean | 5.3 |
| (pooled) | | Std. Dev. | 1.3 |
| | | Sample Size | 18 |
| Patellar Groove | 4 weeks | Mean | 6.6 |
| Defects | | Std. Dev. | 1.0 |
| 20 mins. ultrasound | | Sample Size | 12 |
| Control | | Mean | 5.0 |
| (paired) | | Std. Dev. | 1.5 |
| | | Sample Size | 12 |
| Patellar Groove | 8 weeks | Mean | 7.0 |
| Defects | | Std. Dev. | 1.2 |
| 20 mins. ultrasound (paired) | | Sample Size | 11 |
| Control | | Mean | 5.8 |
| (paired) | | Std. Dev. | 1.4 |
| | | Sample Size | 11 |
| Patellar Groove | 12 weeks | Mean | 6.5 |
| Defects | | Std. Dev. | 1.1 |
| 20 mins. ultrasound (paired) | | Sample Size | 11 |
| Control | | Mean | 5.6 |
| (paired) | | Std. Dev. | 1.1 |
| | | Sample Size | 11 |
| Patellar Groove | 24 weeks | | |
| Defects | | ONGOING | |
| 20 mins. ultrasound for first 12 weeks postoperative | | | |
| Control | | | |
| (paired) | | | |
| Patellar Groove | 24 weeks | | |
| Defects | | ONGOING | |
| 20 mins. ultrasound for first 18 weeks postoperative | | | |
| Control | | | |
| (paired) | | | |

It will be understood that various modifications can be made to the various embodiments of the present invention herein disclosed without departing from its spirit and scope. For example, various modifications may be made in the structural configuration of the placement modules and the configuration of the components used to excite the ultrasonic transducer. Therefore, the above description should not be construed as limiting the invention but merely as presenting preferred embodiments of the invention. Those skilled in the art will envision other modifications within the scope and spirit of the present invention as defined by the claims presented below.

What is claimed is:

1. A kit for ultrasonically stimulating cartilage growth, which comprises:

means for initiating a biological healing response at or adjacent a cartilaginous site;

an ultrasonic transducer assembly having at least one ultrasonic transducer;

a placement module configured to be worn by a patient, said placement module being configured to receive said transducer assembly such that when said placement module is worn said at least one ultrasonic transducer is positioned in proximity to the channels;

an ultrasonic signal generator positioned in said ultrasonic transducer assembly; and a main operating unit.

2. The kit according to claim 1, wherein the means for initiating the biological healing response includes a drill assembly.

3. The kit according to claim 1, wherein the means for initiating the biological healing response includes a laser drill assembly.

4. The kit according to claim 1, wherein the means for initiating the biological healing response includes a scraping assembly.

5. The kit according to claim 1, wherein the means for initiating the biological healing response includes a chemical substance for irradiating the cartilaginous site.

6. The kit according to claim 1, wherein said ultrasonic signal generator includes signal generator circuitry and an internal power source connected to said signal generator circuitry, a display coupled to said signal generator circuitry to display treatment sequence data, and said signal generator circuitry including a processor and means for generating a pulsed RF signal.

7. The kit according to claim 1, further comprising safety interlock means to prevent inadvertent excitation of said at least one ultrasonic transducer.

8. The kit according to claim 1, wherein said placement module includes a locking mechanism which when worn by the patient prevents the patient from bending or extending the limbs.

9. The kit according to claim 1, wherein the placement module is constructed from a conductive material and said at least one ultrasonic transducer is provided on said placement module is electrically coupled to said main operation unit via said conductive material.

10. The kit according to claim 1, wherein the placement module is custom molded for a particular joint of the patient.

11. The kit according to claim 1, wherein at least one ultrasonic transducer includes means for receiving reflected diagnostic data.

12. A method for ultrasonically stimulating a healing response for the regeneration of cartilage comprising the following steps:

initiating a biological healing response at or adjacent a cartilaginous site;

providing a main operating unit having an internal power source coupled to an ultrasonic transducer assembly, said ultrasonic transducer assembly includes at least one ultrasonic transducer, an ultrasonic signal generator and signal generator circuitry therein;

providing a placement module configured to receive said transducer assembly such that when said placement module is secured to a patient's body said at least one ultrasonic transducer is positioned in proximity to the channels; and exciting said at least one ultrasonic transducer to impinge ultrasonic waves towards the cartilaginous site.

13. The method according to claim 12, wherein the step of initiating the biological healing response includes drilling at least one channel within the bone joint walls at the cartilaginous site.

14. The method according to claim 12, wherein the step of initiating the biological healing response is selected from the group consisting of scraping the cartilaginous site, applying a chemical substance to the cartilaginous site, and inducing a fracture at the cartilaginous site.

15. The method according to claim 12, further comprising the step of transplanting non-weight bearing cartilage to the cartilaginous site prior to treatment.

16. The method according to claim 12, further comprising the step of transplanting autologous cultured chondrocytes to the cartilaginous site prior to treatment.

17. The method according to claim 12, further including the step of receiving reflected diagnostic data by said at least one ultrasonic transducer.

18. The method according to claim 12, wherein the step of exciting said at least one ultrasonic transducer to impinge ultrasonic waves towards the cartilaginous site causes the regenerated cartilage to integrate with the non-regenerated cartilage present at the cartilaginous site.

19. A method for ultrasonically stimulating a healing response for the regeneration of cartilage comprising the following steps:

initiating a biological healing response at or adjacent a cartilaginous site;

releasably securing at least one ultrasonic transducer coupled to a signal generator to a band;

affixing the band on a patient such that said at least one transducer is in proximity to an area where the regeneration of cartilage is desired; and exciting said at least one ultrasonic transducer by actuating said signal generator to impinge ultrasonic waves towards the cartilaginous site.

20. The method according to claim 19, further including the step of:

connecting said at least one ultrasonic transducer to an operating unit, said operating unit having an internal power source.

21. The method according to claim 19, further including the step of receiving reflected diagnostic data by said at least one ultrasonic transducer.

* * * * *